US008728765B2

(12) United States Patent
Ching et al.

(10) Patent No.: US 8,728,765 B2
(45) Date of Patent: *May 20, 2014

(54) CLOSED-SYSTEM MULTI-STAGE NUCLEIC ACID AMPLIFICATION REACTIONS

(75) Inventors: Jesus Ching, San Jose, CA (US); Ronald Chang, Redwood City, CA (US); Douglas Dority, Mill Valley, CA (US); Jian Ping Zhang, Moraga, CA (US); James Jian Quan Wang, Fremont, CA (US); Wendy Wong, Mountain View, CA (US); Kendra Lara Paul, Santa Clara, CA (US); Reuel Van Atta, Palo Alto, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/397,416

(22) Filed: Feb. 15, 2012

(65) Prior Publication Data

US 2012/0244534 A1 Sep. 27, 2012

Related U.S. Application Data

(63) Continuation of application No. 11/262,523, filed on Oct. 27, 2005, now Pat. No. 8,133,703.

(60) Provisional application No. 60/622,393, filed on Oct. 27, 2004.

(51) Int. Cl.
  *C12P 19/34* (2006.01)
(52) U.S. Cl.
  USPC .......................................................... 435/91.2
(58) Field of Classification Search
  None
  See application file for complete search history.

(56) References Cited

U.S. PATENT DOCUMENTS

| 5,229,297 | A | 7/1993 | Schnipelsky et al. |
| 5,556,773 | A | 9/1996 | Youmo et al. |
| 6,235,471 | B1 | 5/2001 | Knapp et al. |
| 6,374,684 | B1 | 4/2002 | Dority |

(Continued)

FOREIGN PATENT DOCUMENTS

| WO | 00/78455 | 12/2000 |
| WO | 01/84463 | 11/2001 |
| WO | 2004/065010 | 8/2004 |

OTHER PUBLICATIONS

Sullivan, Kevin M., et al., "Automated Amplification and Sequencing of Human Mitochondrial DNA," 1991 *Electrophoresis*, vol. 12, pp. 17-21.

(Continued)

*Primary Examiner* — Suchira Pande
(74) *Attorney, Agent, or Firm* — Kilpatrick Townsend & Stockton LLP

(57) ABSTRACT

The invention is directed to systems, methods, and apparatus for carrying out multi-stage amplification reactions, especially under fluidly closed conditions. In one aspect, methods of the invention are carried out in a fluidly closed reaction system that permits the isolation of a portion of a first (or prior) reaction mixture and its use as a sample or specimen in a second (or subsequent) reaction mixture, thereby substantially avoiding interfering effects that first reaction components may have in the second reaction if both reaction mixtures were simply combined together. In this aspect, systems, methods, and apparatus of the invention may be used with any amplification reaction that permits multiple stages of amplification based on the use of nested primers.

11 Claims, 13 Drawing Sheets

(56) References Cited

U.S. PATENT DOCUMENTS 6,569,627 B2    5/2003    Wittwer et al.
6,748,975 B2 *  6/2004    Hartshorne et al. ..... 137/625.46
6,818,185 B1    11/2004   Peterson et al.
6,960,437 B2    11/2005   Enzelberger et al.
8,133,703 B2 *  3/2012    Ching et al. ................. 435/91.2

2005/0233314 A1    10/2005    Juang et al.

OTHER PUBLICATIONS

Anonymous Disclosure: "PCR Processor," Apr. 1997, Research Disclosure Database [online] RD: Database Accession No. 396004.

* cited by examiner

CLOSED-SYSTEM MULTI-STAGE NUCLEIC ACID AMPLIFICATION REACTIONS

CROSS-REFERENCES TO RELATED APPLICATIONS

This application is a continuation of U.S. patent application Ser. No. 11/262,523, filed Oct. 27, 2005, now U.S. Pat. No. 8,133,703, which claims the benefit of U.S. Provisional Patent Application No. 60/622,393, filed Oct. 27, 2004, the entire disclosure of each of the above is incorporated herein by reference.

BACKGROUND OF THE INVENTION

The invention relates generally to systems and methods for analyzing a sample for the presence of one or more nucleic acids, and more particularly, to systems and methods for conducting multi-stage nucleic acid amplification reactions, especially polymerase chain reactions (PCRs), under closed conditions.

Nucleic acid amplification reactions are crucial for many research, medical, and industrial applications. Such reactions are used in clinical and biological research, detection and monitoring of infectious diseases, detection of mutations, detection of cancer markers, environmental monitoring, genetic identification, detection of pathogens in biodefense applications, and the like, e.g. Schweitzer et al., Current Opinion in Biotechnology, 12: 21-27 (2001); Koch, Nature Reviews Drug Discovery, 3: 749-761 (2004). In particular, polymerase chain reactions (PCRs) have found applications in all of these areas, including applications for viral and bacterial detection, viral load monitoring, detection of rare and/or difficult-to-culture pathogens, rapid detection of bio-terror threats, detection of minimal residual disease in cancer patients, food pathogen testing, blood supply screening, and the like, e.g. Mackay, Clin. Microbiol. Infect., 10: 190-212 (2004); Bernard et al., Clinical Chemistry, 48: 1178-1185 (2002). In regard to PCR, key reasons for such widespread use are its speed and ease of use (typically performed within a few hours using standardized kits and relatively simple and low cost instruments), its sensitivity (often a few tens of copies of a target sequence in a sample can be detected), and its robustness (poor quality samples or preserved samples, such as forensic samples or fixed tissue samples are readily analyzed), Strachan and Read, Human Molecular Genetics 2 (John Wiley & Sons, New York, 1999).

Despite the advances in nucleic acid amplification techniques that are reflected in such widespread applications, there is still a need for further improvements in speed and sensitivity, particularly in such areas as infectious disease detection, minimum residual disease detection, bio-defense applications, and the like.

Significant improvements in sensitivity of PCRs have been obtained by using nested sets of primers in a two-stage amplification reaction, e.g. Albert et al., J. Clin. Microbiol., 28: 1560-1564 (1990). In this approach, the amplicon of a first amplification reaction becomes the sample for a second amplification reaction using a new set of primers, at least one of which binds to an interior location of the first amplicon. While increasing sensitivity, the approach suffers from increased reagent handling and increased risk of introducing contaminating sequences, which can lead to false positives. Attempts have been made to overcome these obstacles with so-called closed-tube nested PCRs; however, such approaches rely primarily on schemes for sequestering reagents in different sections of the same reaction vessel such that a second-stage reaction may be initiated by forcing reagents together by some physical process, such as centrifugation, e.g. Yourno, PCR Methods and Applications, 2: 60-65 (1992); Wolff et al., PCR Methods and Applications, 4: 376-379 (1995); Olmos et al., Nucleic Acids Research, 27: 1564-1565 (1999). Thus, substantial portions of first-stage reaction components are present in the second-stage reaction.

Significant improvements in sensitivity and a reduction of false positives have also been obtained by carrying out reactions in closed environments. A drawback of highly sensitive amplification techniques is the occurrence of false-positive test results, caused by inappropriate amplification of non-target sequences, e.g. Borst et al., Eur. J. Clin. Microbiol. Infect. Dis., 23: 289-299 (2004). The presence of non-target sequences may be due to lack of specificity in the reaction, or to contamination from prior reactions (i.e. "carry over" contamination) or to contamination from the immediate environment, e.g. water, disposables, reagents, etc. Such problems can be ameliorated by carrying out amplifications in closed vessels, so that once a sample and reagents are added and the vessel sealed, no further handling of reactants or products takes place. Such operations have been made possible largely by the advent of "real-time" amplifications that employ labels that continuously report the amount of a product in a reaction mixture.

Despite the attempts at multi-stage amplifications in closed vessels, the current art lacks methods or systems in which multi-stage reactions can take place without the possibility of there being interfering effects from undesired components, e.g. primers or other components, of prior reactions. Accordingly, there remains a need for new approaches for carrying out closed multi-stage amplification reactions that have the convenience of single-stage techniques, but which have the greater sensitivity afforded by a multi-stage amplification using nested primers.

BRIEF SUMMARY OF THE INVENTION

The present invention provides systems, methods, and apparatus for closed multi-stage nucleic acid amplification reactions wherein a portion of a prior-stage reaction mixture serves as the sample for the next stage reaction.

In one aspect, the invention provides a method of detecting the presence or absence of one or more target polynucleotides in a sample having the following steps: (a) amplifying in a fluidly closed reaction system one or more target polynucleotides from a sample using first-stage amplification reagents in a first reaction mixture to form one or more first amplicons, the first-stage amplification reagents including initial primers for each target polynucleotide; (b) isolating a sample of the first reaction mixture in the fluidly closed reaction system; and (c) amplifying in the fluidly closed reaction system the one or more first amplicons in the sample using second-stage amplification reagents in a second reaction mixture to form one or more second amplicons, the second-stage amplification reagents including at least one secondary primer for each of the one or more first amplicons, such that each second primer is nested in such first amplicon relative to an initial primer of such first amplicon.

In another aspect, the invention provides a method of controlling a nested amplification reaction comprising the step of (i) amplifying in a first-stage amplification reaction a target polynucleotide in the presence of a fluorescent indicator in a reaction mixture, the fluorescent indicator being capable of generating an optical signal related to a quantity of an amplicon in the first-stage amplification reaction; (ii) monitoring the optical signal of the fluorescent indicator in the first-stage amplification reaction; and (iii) automatically separating an effective portion of the reaction mixture of the first-stage amplification reaction to initiate a second-stage amplification reaction whenever the optical signal reaches or exceeds a predetermined level.

In another aspect, the invention provides a method of detecting presence or absence of one or more target polynucleotides in a sample, the method comprising the steps of: (i) providing a reaction chamber selectably in fluid communication with a waste reservoir, a sample reservoir containing a sample, a first reactant reservoir containing first-stage amplification reagents, and a second reactant reservoir containing second-stage amplification reagents, each of said reservoirs being fluidly closed; (ii) fluidly transferring sample from the sample reservoir and first-stage amplification reagents from the first reactant reservoir to the reaction chamber so that the first-stage amplification reagents react with the sample in an amplification reaction to produce a reaction product containing a first amplicon whenever a target polynucleotide is present in the sample; (iii) fluidly transferring the reaction product to the waste reservoir, except for an effective portion that remains in the reaction chamber; (iv) fluidly transferring second-stage amplification reagents from the second reactant reservoir to the reaction chamber so that the second-stage amplification reagents react with the effective portion of the reaction product in an amplification reaction to produce a second amplicon whenever the first amplicon is present in the reaction product; and (v) detecting the second amplicon to determine whether the target polynucleotide is present in the sample.

In another aspect, the invention provides a method for determining relative amounts of one or more target polynucleotides in a sample, the method comprising the steps of: (i) amplifying in the sample the one or more target polynucleotides and at least one reference sequence in a first amplification reaction to form a first reaction product including a first amplicon for each target polynucleotide and reference sequence, the first amplification reaction including initial primers for each target polynucleotide and reference sequence; (ii) amplifying in a second amplification reaction first amplicons of the one or more target polynucleotides from an effective portion of the first reaction product to form a second amplicon for each first amplicon, the second amplification reaction including secondary primers for each target polynucleotide such that each secondary primer of each first amplicon is nested in such first amplicon relative to the initial primers thereof; and (iii) comparing second amplicons of the second amplification reaction to amplicons of the at least one reference sequence in the first amplification reaction to determine relative amounts of the one or more target polynucleotides in the sample.

In another aspect of the invention, a fluidly closed reaction system is provided for performing a nested amplification reaction, the system comprising: (i) a reaction chamber selectably in fluid communication with a sample reservoir containing a sample, a waste reservoir, a first reactant reservoir containing first-stage amplification reagents, and a second reactant reservoir containing second-stage amplification reagents, each of said reservoirs being fluidly closed; and (ii) a pump operationally associated with a rotary valve for fluidly transferring the sample and the first-stage amplification reagents to the reaction chamber, wherein a first amplification reaction is performed to form one or more first amplicons in a reaction mixture; for isolating an effective portion of the reaction mixture; and for fluidly transferring said second-stage amplification reagents and the effective portion to the reaction chamber, wherein a second amplification is performed to form one or more second amplicons.

In another aspect, the invention provides a reaction vessel comprising for carrying out methods of the invention, the reaction vessel comprising: (i) a reaction chamber for containing a liquid; (ii) an inlet port connected to the reaction chamber by an inlet channel; (iii) an outlet port connected to the reaction chamber by an outlet channel; and (iv) a retaining member in the reaction chamber, the retaining member being positioned to retain a defined volume of the liquid in the reaction chamber whenever the remainder of the liquid is removed from the reaction chamber through the outlet channel.

In another aspect, the invention provides an apparatus for performing a multi-stage reaction, the apparatus comprising: (a) a body having at least first and second channels formed therein; and (b) a reaction vessel extending from the body, the reaction vessel comprising: (i) a reaction chamber for containing a liquid; (ii) an inlet port connected to the reaction chamber by an inlet channel; (iii) an outlet port connected to the reaction chamber by an outlet channel; and (iv) a retaining member in the reaction chamber, the retaining member being positioned to retain a volume of the liquid in the reaction chamber whenever the remainder of the liquid is removed from the reaction chamber through the outlet channel, wherein the inlet port of the vessel is connected to the first channel in the body and wherein the outlet port of the vessel is connected to the second channel in the body.

In still another aspect, the invention provides a computer-readable product embodying a program for execution by a computer to control the performance of a nested amplification reaction, the program comprising instructions for: (a) reading values of an optical signal from a first-stage amplification reaction, the optical signal being monotonically related to a concentration of an amplicon in the first-stage amplification reaction, and the values of the optical signal having a most recent value; (b) determining a baseline signal level from the values of the optical signal; (c) computing a predetermined level from the values of the optical signal; (d) comparing the predetermined value with the most recent value of the optical signal; (e) initiating a second-stage amplification reaction whenever the most recent value of the optical signal is equal to or greater than the predetermined level; and (f) repeating steps (d) and (e) until the second-stage reaction is initiated.

In another aspect, the invention provides a method of amplifying one or more RNA sequences, the method comprising the steps of: (i) transcribing one or more RNA sequences in a fluidly closed reaction system to form one or more complementary single stranded DNA sequences using reverse transcriptase reagents in a first reaction mixture; (ii) isolating a first effective portion of the first reaction mixture in the fluidly closed reaction system; and (iii) amplifying in the fluidly closed reaction system the one or more complementary single stranded DNA sequences in the first effective portion using first-stage amplification reagents in a second reaction mixture to form one or more first amplicons, the first-stage amplification reagents including initial primers for each of the complementary single stranded DNA sequences.

The present invention provides a system and methods for detecting or measuring one or more polynucleotides in a specimen or sample that, in its various aspects, has several advantages over current techniques including, but not limited to, (1) higher sensitivity in two-stage amplification reactions in closed systems by avoidance of "carry over" reactants; (2) performance of real-time multi-stage amplification reactions with closed-loop control of reaction initiation, and more specifically, performance of real-time nested PCR; (3) more accurate quantitation of low abundance target polynucleotides in multi-stage amplifications by single-stage amplification of reference sequences and multi-stage amplification of target sequences; and (4) convenient, disposable reaction vessels for carrying out the methods of the invention.

Definitions

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, $2^{nd}$ Edition (Cold Spring Harbor Laboratory, 1989); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, ligase chain reactions (LCRs), strand-displacement reactions (SDAs), nucleic acid sequence-based amplification (NASBAs), rolling circle amplifications, and the like, disclosed in the following references that are incorporated herein by reference: Mullis et al., U.S. Pat. Nos. 4,683,195; 4,965,188; 4,683,202; 4,800,159 (PCR); Gelfand et al., U.S. Pat. No. 5,210,015 (real-time PCR with "taqman" probes); Wittwer et al., U.S. Pat. No. 6,174,670; Landegren et al., U.S. Pat. No. 4,988,617 ("LCR"); Birkenmeyer et al., U.S. Pat. No. 5,427,930 ("gap-LCR"); Kacian et al., U.S. Pat. No. 5,399,491 ("NASBA"); Walker, U.S. Pat. Nos. 5,648,211; 5,712,124 ("SDA"); Lizardi, U.S. Pat. No. 5,854,033; Aono et al., Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al., Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Closed" in reference to an amplification reaction means that such reaction takes place within a vessel or container or chamber that has no openings through which liquids may pass, in particular, liquids that contain non-sample materials, such as, non-sample biomolecules or organisms, including, but not limited to, nucleic acids, proteins, viruses, bacteria, or the like. In one aspect, a vessel, chamber, or container containing a closed amplification reaction may include a port or vent that is gas permeable but liquid impermeable, for example, a port that permits the venting of air through a filter membrane but not liquids under conventional reaction conditions. Suitable membranes for such ports or vents include woven polyolefin films, such as Tyrek® film (DuPont), or the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Computer-readable product" means any tangible medium for storing information that can be read by or transmitted into a computer. Computer-readable products include, but are not limited to, magnetic diskettes, magnetic tapes, optical disks, CD-ROMs, punched tape or cards, read-only memory devices, direct access storage devices, gate arrays, electrostatic memory, and any other like medium.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Fluidly closed" means that, under conventional operating conditions, liquids within a system that comprises one or more vessels, chambers, valves, and/or passages, possibly interconnected and in communication with one another, cannot communicate with the exterior of such a system, and likewise liquids on the exterior of such a system cannot communicate with liquids contained within the interior of the system. In one aspect, conventional operating conditions means that vessels, chambers, valves, and passages of a fluidly closed system are pressurized to an extent less than 100 psi, or in another aspect, to an extent less than 50 psi, or to an extent less than 30 psi.

"Fluorescent indicator" means a probe that is capable of generating a fluorescent signal in the presence of a product of an amplification reaction (i.e. an "amplification product") such that as product accumulates in the reaction mixture the signal of the fluorescent indicator increases, at least over a predetermined range of concentrations. Fluorescent indicators may be non-specific, such as intercalating dyes that bind to double stranded DNA products, e.g. YO-PRO-1, SYBR green 1, and the like, Ishiguro et al., Anal. Biochem., 229: 207-213 (1995); Tseng et al., Anal. Biochem., 245: 207-212 (1997); Morrison et al., Biotechniques, 24: 954-962 (1998); or such as primers having hairpin structures with a fluorescent molecule held in proximity to a fluorescent quencher until forced apart by primer extension, e.g. Whitecombe et al., Nature Biotechnology, 17: 804-807 (1999) ("Amplifluor™ primers"). Fluorescent indicators also may be target sequence specific, usually comprising a fluorescent molecule in proximity to a fluorescent quencher until an oligonucleotide moiety to which they are attached specifically binds to an amplification product, e.g. Gelfand et al., U.S. Pat. No. 5,210,015 ("taqman"); Nazarenko et al., Nucleic Acids Research, 25: 2516-2521 (1997) ("scorpion probes"); Tyagi et al., Nature Biotechnology, 16: 49-53 (1998) ("molecular beacons"). Fluorescent indicators may be used in connection with real-time PCR, or they may be used to measure the total amount of reaction product at the completion of a reaction.

"Internal standard" means a nucleic acid sequence that is amplified in the same amplification reaction as a target polynucleotide in order to permit absolute or relative quantification of the target polynucleotide in a sample. An internal standard may be endogenous or exogenous. That is, an internal standard may occur naturally in the sample, or it may be added to the sample prior to amplification. In one aspect, multiple exogenous internal standard sequences may be added to a reaction mixture in a series of predetermined concentrations to provide a calibration to which a target amplicon may be compared to determine the quantity of its corresponding target polynucleotide in a sample. Selection of the number, sequences, lengths, and other characteristics of exogenous internal standards is a routine design choice for one of ordinary skill in the art. Preferably, endogenous internal standards, also referred to herein as "reference sequences," are sequences natural to a sample that correspond to minimally regulated genes that exhibit a constant and cell cycle-independent level of transcription, e.g. Selvey et al., Mol. Cell Probes, 15: 307-311 (2001). Exemplary reference sequences include, but are not limited to, sequences from the following genes: GAPDH, $\beta_2$-microglobulin, 18S ribosomal RNA, and $\beta$-actin (although see Selvey et al., cited above).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool, Nucleic Acids Research, 27: 875-881 (1999); Higgins et al., Methods in Enzymology, 68: 50-71 (1979); Engler et al., The Enzymes, 15: 3-29 (1982); and Namsaraev, U.S. patent publication 2004/0110213.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, and a detection system. Microfluidics may further include valves, pumps, and specialized functional coatings on their interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 1000 µm to about 0.1 µm. Microfluidics devices typically have volume capacities in the range of from 100 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al., U.S. Pat. Nos. 5,126,022 and 6,054,034; Nelson et al., U.S. Pat. No. 6,613,525; Maher et al., U.S. Pat. No. 6,399,952; Ricco et al., International patent publication WO 02/24322; Bjornson et al., International patent publication WO 99/19717; and Wilding et al., U.S. Pat. Nos. 5,587,128; 5,498,392.

"Nucleoside" as used herein includes the natural nucleosides, including 2'-deoxy and 2'-hydroxyl forms, e.g. as described in Kornberg and Baker, DNA Replication, $2^{nd}$ Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., Exp. Opin. Ther. Patents, 6: 855-870 (1996); Mesmaeker et al., Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al., U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al., U.S. Pat. No. 5,210,015 ("taqman"); Wittwer et al., U.S. Pat. Nos. 6,174,670 and 6,569,627 (intercalating dyes); Tyagi et al., U.S. Pat. No. 5,925,517 (molecular beacons); which patents are incorporated herein by reference. Detection chemistries for real-time PCR are reviewed in Mackay et al., Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al., Anal. Biochem., 273: 221-228 (1999) (two-color real-time PCR). Usually, distinct sets of primers are employed for each sequence being amplified. Typically, the number of target sequences in a multiplex PCR is in the range of from 2 to 10, or from 2 to 6, or more typically, from 2 to 4.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $\beta_2$-microglobulin, ribosomal RNA, and the like. Techniques for quantitative PCR are well-known to those of ordinary skill in the art, as exemplified in the following references that are incorporated by reference: Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989); and the like.

"Polynucleotide" and "oligonucleotide" are used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Diefenbach, editor, PCR Primer: A Laboratory Manual, $2^{nd}$ Edition (Cold Spring Harbor Press, New York, 2003).

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Tm" or "melting temperature" means the temperature at which a population of double-stranded nucleic acid molecules becomes half dissociated into single strands. Several equations for calculating the Tm of nucleic acids are well known in the art. For example, a simple estimate of the Tm value may be calculated by the equation. $Tm=81.5+0.41$ (% G+C), when a nucleic acid is in aqueous solution at 1 M NaCl. Methods for calculating Tm based on more complete models of duplex formation and dissociation are found in Breslauer et al., Proc. Natl. Acad. Sci., 83: 3746-3750 (1986); and Wetmur, Crit. Rev. Biochem. Mol. Biol., 26: 227-259 (1991).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

"Spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photo-detection systems, e.g. employing a system of band pass filters and photomultiplier tubes, or the like, as exemplified by the systems described in U.S. Pat. Nos. 4,230,558; 4,811,218, or the like, or in Wheeless et al., pgs. 21-76, in Flow Cytometry: Instrumentation and Data Analysis (Academic Press, New York, 1985).

DETAILED DESCRIPTION OF THE INVENTION

Figure 1A:
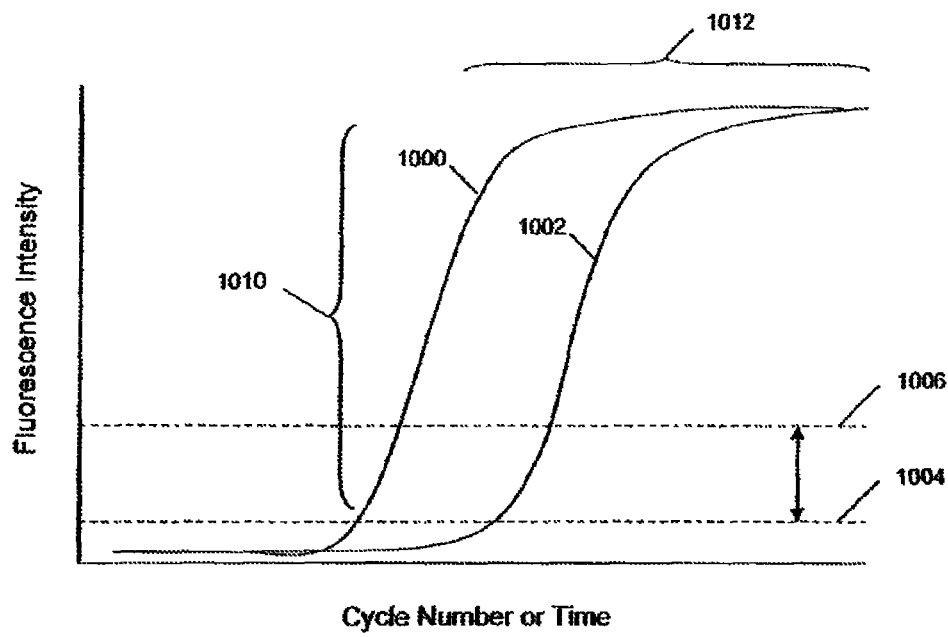
FIGS. 1A-1B illustrate signal v. cycle number (or reaction time) curves for amplification reactions, such as real-time PCRs.

The invention is directed to systems, methods, and apparatus for carrying out multi-stage amplification reactions, especially under fluidly closed conditions. In one aspect, methods of the invention are carried out in a fluidly closed reaction system that permits the isolation of a portion of a first (or prior) reaction mixture and its use as a sample or specimen in a second (or subsequent) reaction mixture, thereby substantially avoiding interfering effects that first reaction components may have in the second reaction if both reaction mixtures were simply combined together. In this aspect, systems, methods, and apparatus of the invention may be used with any amplification reaction that permits multiple stages of amplification based on the use of nested primers.

In particular, they are well-suited for carrying out two-stage, or nested, PCRs and NASBA reactions. By way of example, basic reaction conditions for nested PCRs and NASBA reactions are described below; however, one of ordinary skill in the art would appreciate that the same principle of using nested primers in PCRs or NASBA reactions to achieve greater sensitivity may be applied similarly in other amplification reactions using one or more primers. In another aspect the invention also provides for two-stage RT-PCR reactions in fluidly closed reaction systems, wherein a second stage PCR may be performed without components of the RT reaction affecting the subsequent PCR, e.g. Sellner et al., Nucleic Acids Research, 20: 1487 (1992). In a further aspect, the invention provides a three-stage reaction wherein a reverse transcriptase reaction is performed to convert one or more RNA targets into one or more complementary single stranded DNAs that, in turn, are amplified in a two-stage amplification reaction, such as a reverse transcriptase-nested PCR, or "RT-nPCR."

As mentioned above, in one aspect of the invention, an apparatus is provided for conducting a two-step reaction, such apparatus comprising: a) a body having at least first and second channels formed therein; and b) a reaction vessel extending from the body, the reaction vessel having: i) a reaction chamber for receiving liquid; ii) an inlet port connected to the reaction chamber via an inlet channel; iii) an outlet port connected to the reaction chamber via an outlet channel; and iv) a retaining member in the reaction chamber, the retaining member being positioned to retain a defined portion of the liquid in the reaction chamber while the remainder of the liquid is removed through the outlet channel, wherein the inlet port of the vessel is connected to the first channel in the body and wherein the outlet port of the vessel is connected to the second channel in the body. The apparatus of the invention further includes a vent in fluid communication with the second channel for venting gas from the second channel.

The apparatus of the invention further comprises a differential pressure source for forcing fluid in the first channel in the body to flow through the inlet port of the vessel and into the reaction chamber. The vessel of the invention further includes: i) a rigid frame defining side walls of the reaction chamber; and ii) first and second polymeric films attached to opposite sides of the rigid frame to form opposing major walls of the reaction chamber. The body of the apparatus further includes a mixing chamber for mixing a fluid sample with amplification reagents, the mixing chamber being connected to the inlet port of the vessel via the first channel. The body of the apparatus further includes a waste chamber for receiving the remainder of the liquid removed through the outlet channel, the waste chamber being connected to the outlet port of the vessel via the second channel. The body of the apparatus further has formed therein: i) a sample flow path; and ii) a separation region in the sample flow path for separating a desired analyte from a fluid sample, the separation region being connected to the inlet port of the vessel via the first channel. In one aspect, the separation region in the body comprises: a) a lysing chamber in the sample flow path for lysing cells or viruses in the sample to release material therefrom; and b) at least one solid support positioned in the lysing chamber for capturing the cells or viruses to be lysed. The vessel of the apparatus includes a plurality of walls defining the reaction chamber, at least one of the walls comprising a flexible sheet or film, and the apparatus further comprises: a) at least one thermal surface for contacting the sheet or film; b) means for increasing the pressure in the reaction chamber, wherein the pressure increase in the chamber is sufficient to force the sheet or film to conform to the thermal surface; and c) at least one thermal element for heating or cooling the surface to induce a temperature change within the chamber.

The vessel of the apparatus further includes two opposing major walls and sidewalls connecting the major walls to each other to form the reaction chamber, at least two of the side walls are optically transmissive and angularly offset from each other, and the apparatus further comprises an optics system having at least one light source for transmitting light to the reaction chamber through a first one of the optically transmissive side walls and having at least one detector for detecting light emitted from the chamber through a second one of the optically transmissive side walls.

Nested Amplification Reactions

As mentioned above in regard to PCRs, nested amplification reactions are multi-stage reactions in which an amplicon of a prior stage serves as a sample for a successive stage using a new primer or pair of primers that bind to at least one interior location in the earlier-produced amplicon. Within each stage of a nested amplification reaction, the amplification reaction proceeds in a conventional fashion. Design choices for concatenating individual amplification reactions into a nested amplification reaction include the following: (i) the number of cycles or duration of each stage, (ii) the size of an effective portion of a first-stage reaction mixture for serving as the sample for a second-stage reaction, (iii) selection of the interior binding site(s) for second-stage primers, (iv) whether reference sequences should be amplified in each stage, (v) whether the same kind of amplification reaction should be run in each stage, e.g. for two-stage nested amplification reactions: PCR-PCR, NASBA-NASBA, PCR-NASBA, and the like. Usually nested amplification reactions are either successive PCRs or successive NASBA reactions and are carried out under conventional reaction conditions.

In one aspect of the invention, when a PCR is one stage of a nested amplification reaction, the number of cycles in the PCR is in the range of from 20 to 40, or in the range of from 24 to 36. In another aspect, the number of cycles is a number sufficient to produce a predeterminable amount of amplicon, which, in turn, produces a predetermined signal in a real-time signal-generation chemistry. If a nested amplification reaction comprises two successive PCRs, the number of cycles and other reaction conditions in the successive PCRs may be the same or different.

For a first, or prior, stage reaction, in one aspect, an effective portion is an amount sufficient to permit the initiation of a second-stage reaction. In one aspect, an effective portion is an amount sufficient to provide in a second-stage reaction a target concentration of at least 1 target polynucleotides per $\mu L$, or in another aspect, at least 10 target polynucleotides per $\mu L$, or in another aspect, at least 50 target polynucleotides per $\mu L$, or in another aspect at least 100 target polynucleotides per $\mu L$, or in another aspect, at least 500 target polynucleotides per $\mu L$, or in another aspect, at least 1000 target polynucleotides per $\mu L$. In still another aspect, an effective portion is an amount that is from 0.5 to 10 percent of the volume of the first-stage reaction mixture, or an amount that is from 1 to 5 percent of the volume of the first-stage reaction mixture. As noted below, in some embodiments, in order to withdraw an effective portion with greater accuracy and to minimize sampling error, a first-stage reaction mixture is diluted prior to removal or isolation of a portion. For example, to obtain a 10 percent portion of a first-stage reaction mixture having a volume of 1 $\mu L$, one may dilute to 10 $\mu L$ followed by removal of 1 $\mu L$ of the diluted mixture, instead of directly removing 0.1 $\mu L$ from the undiluted mixture. Generally, the reactants in a second-stage amplification reaction may be the same as those in the first-stage reaction, with at least the following exception: one or more primers are distinct in the second-stage reaction, but concentrations of primers in the second-stage reaction are conventional. Signal generating schemes in the first-stage and second-stage amplification reactions may be the same or different.

In one aspect, the invention provides a method for automatically initiating a second-stage (or subsequent-stage) amplification reaction, either under open-loop control or closed-loop control. In embodiments with open-loop control, a first-stage amplification reaction is carried out for a predetermined number of cycles or for a predetermined reaction time, after which an effective portion of the reaction mixture is isolated, combined with second stage reactants, and a second-stage amplification reaction is initiated. In such embodiments, real-time monitoring of the first-stage amplicons is optional. In embodiments with closed-loop control, a reaction parameter of a first-stage amplification reaction is monitored and when it takes on a predetermined value, or crosses a predetermined threshold value, the first-stage reaction is stopped, an effective portion of the reaction mixture is isolated, combined with second stage reactants, and a second-stage amplification reaction is initiated. The reaction parameter used for determining when to initiate the second-stage amplification may be any parameter that has a well-defined relationship with the accumulation of reaction products, or in other words, with the degree of completion of such first-stage reaction. Preferably, the reaction parameter has a monotonic relationship with the accumulation of one or more products in the first-stage reaction, so that increasing values of the parameter may be either positively or negatively correlated with the amount(s) of such products, which are usually one or more amplicons. Reaction parameters may include, but are not limited to, optical density of the reaction mixture; temperature; pH; concentration of secondary reaction products; amplicon concentration, the latter, for example, being based on one or more fluorescent signals, colorimetric signals, chemiluminescent signals, electrochemiluminescent signals, or electrochemical signals; and the like. In one aspect, a reaction parameter is monotonically related to the concentration of at least one amplicon in the first-stage reaction. Such an amplicon may be produced from a target polynucleotide, or a reference sequence or other internal standard. Thus, in a nested PCR with closed-loop control, the first-stage amplification reaction is a real-time PCR. In one aspect of the invention, the reaction parameter is an amplicon detected by a fluorescent indicator whose signal is monotonically related to the concentration of the amplicon in the reaction mixture. Where there is variability in the amount or quality of target nucleic acid in a sample or specimen, closed-loop control of the second-stage reaction can produce more consistent and less variable readout.

Since in some applications, a sample may or may not contain a target polynucleotide. Thus, in one aspect, the amplicon of one or more reference sequences, or other internal standard, is monitored for determining when to initiate a second-stage reaction. That is, such an internal standard serves as a positive control and reaction parameter for initiating a second-stage reaction. In another aspect, both amplicons of an internal standard and of a target polynucleotide must reach or exceed predetermined levels, which may be the same or different, in order to initiate a second-stage reaction.

In another aspect of the invention, when a first-stage amplification reaction is a PCR under open-loop control, the number of cycles carried out prior to initiation of a second-stage reaction is in the range of between 20 and 40, or in another aspect, in the range of between 20 and 30. In another aspect, when a first-stage amplification reaction is stopped and a second-stage amplification reaction is initiated after a predetermined time, the predetermined time may be selected empirically for the particular type of sample that is being analyzed. For example, in samples having reference sequences, a predetermined time may be selected as the average time it takes to amplify a selected reference sequence to some fraction, e.g. quarter, third, half, or the like, of its plateau value in an average sample.

Figure 1B:
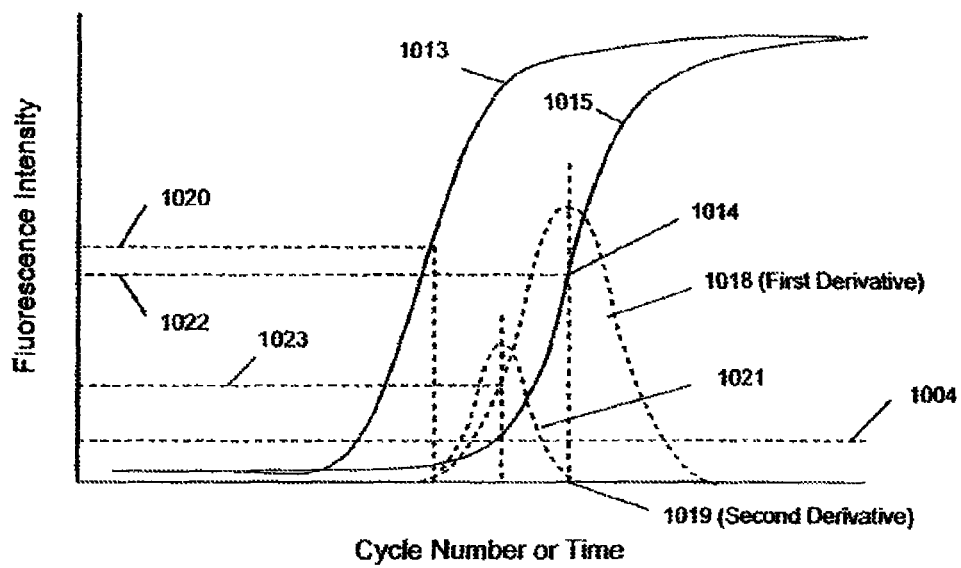

When a first-stage amplification reaction is under closed-loop control, the value of the first-stage reaction parameter at which the second-stage reaction is initiated may be selected in a variety of ways. In one aspect, the value is determined as a function of a baseline signal level, or background noise, value, or as a characteristic of a function that describes the accumulation of one or more amplicons in the reaction mixture, as illustrated in FIGS. 1A and 1B. In FIG. 1A, curves (1000) and (1002) represent accumulated amplicon of, for example, a reference sequence and target polynucleotide, respectively, as determined by two different fluorescent signals generated by amplicon-specific probes, e.g. molecular beacons having fluorescent dyes that emit fluorescence at distinguishable wavelengths. Such curves are typically sigmoid as illustrated, each having a region of low positive slope below a noise level, or baseline signal, (1004), a log-linear region (1010) of high positive slope, and a plateau region (1012) of low positive slope that corresponds to the stage in the reaction where reactants become exhausted and/or interfering side products accumulate. In one aspect of the invention, a second-stage reaction is initiated when curve (1002) of the target amplicon reaches or exceeds a predetermined level (1006), which may be a function of baseline signal (1004). In another aspect, a second-stage reaction is initiated when both curve (1002) of the target amplicon and curve (1000) of a reference sequence both reach or exceed a predetermined level (1006). Selection of predetermined level (1006) is a routine design choice for one of ordinary skill in the art that may depend on a variety of factors, e.g. the likelihood of sequences closely related to the target being amplified in the first-stage reaction (i.e. lack of specificity in an assay), the quality of the sample and the extent to which it contributes to the baseline signal value, the type of amplification reaction used, the signal detection system employed, and the like. In one aspect, predetermined level (1006) is a multiple of baseline signal value (1004). By way of example, predetermined level (1006) may be selected from a range between 1.5 and 25 times a baseline signal value. In another aspect, predetermined level (1006) is 1.5 times the baseline signal value, or 2 times the baseline signal value, or 3 times the baseline signal value, or 5 times the baseline signal value, or 10 times the baseline signal value. A baseline signal value may be a function, e.g. an average, of fluorescent measurements of a predetermined number of cycles, or for a predetermined time interval, near the beginning of an amplification reaction. The fluorescent measurements may be, or include, measurements of signals from the same channel as that for the fluorescent signal generated by the amplicon being monitored. In one aspect, a baseline signal value is a function of the initial 10, or 25, or 50, or 100 optical signal values measured for at least one amplicon growth curve. In one aspect, such function is an arithmetic average of such initial optical signal values. Preferably, predetermined level (1006) intersects curve (1002) and/or curve (1000) in their respective log-linear regions (1010). Amplicons may be identified and/or measured with a variety of labels that generate optical signals, including but not limited to fluorescent indicators, colorimetric labels, chemiluminescent labels, electrochemiluminescent labels, and the like.

In another aspect, the value of a reaction parameter at which a second-stage reaction is initiated may be determined by a characteristic of a curve describing the relationship of an accumulated amplicon and cycle number or time in an amplification reaction, as illustrated in FIG. 1B (referred to herein as an "amplicon growth curve"). As in FIG. 1A, curve (1013) and curve (1015) describe the accumulation of amplicons corresponding to a reference sequence and a target polynucleotide, respectively. Both curves at each point have positive slopes, however, the magnitude of the slopes changes from early in the reaction to late in the reaction, with the slopes being flat in the beginning, steep in the log-linear region, and flat again in the plateau region. If the derivative is taken of such a curve, a roughly symmetrical function (1018) is produced that has a maximum at time or cycle value (1019). Value (1019) is a root of the first derivative of curve (1015). Value (1019) corresponds to the point (1014) at which the slope of curve (1015) stops increasing and starts decreasing, that is, it is an inflexion point, which is located in approximately the middle of the log-linear region, which makes it an attractive characteristic of curve (1015) for determining a signal value (1022) at which to initiate a second-stage reaction. In another aspect, a second derivative of curve (1015) may be determined to produce another roughly symmetrical function illustrated by curve (1021). The root of curve (1021) provides another candidate characteristic for determining a signal value, e.g. (1023), at which to initiate a second-stage reaction. Determination of signal values corresponding to such characteristics of curves (1015) describing the accumulation of amplicon is disclosed in McMillan et al., U.S. Pat. No. 6,783,934, which is incorporated herein by reference. As mentioned above, the term "amplicon growth curve" means a curve, such as curves (1000), (1002), (1013), or (1015), that describes the accumulation of amplicon in a reaction mixture as a function of cycle number or time, or as a function of a related parameter, e.g. temperature in a non-temperature regulated amplification reaction, or the like. It is understood that characteristics, such as first or second derivatives, of amplicon growth curves are repeatedly computed during an assay as data making up the curve is collected. It is also understood that because of the real-time nature of the above assays, it may only be possible to determine certain characteristics of an amplicon growth curve retrospectively; thus, such characteristics may not be suitable in every situation for determining when a second-stage amplification reaction should be initiated. Selecting an appropriate characteristic of an amplicon growth curve for determining when to initiate a second-stage amplification reaction is a routine design choice for one of ordinary skill in the art.

Figure 1C:
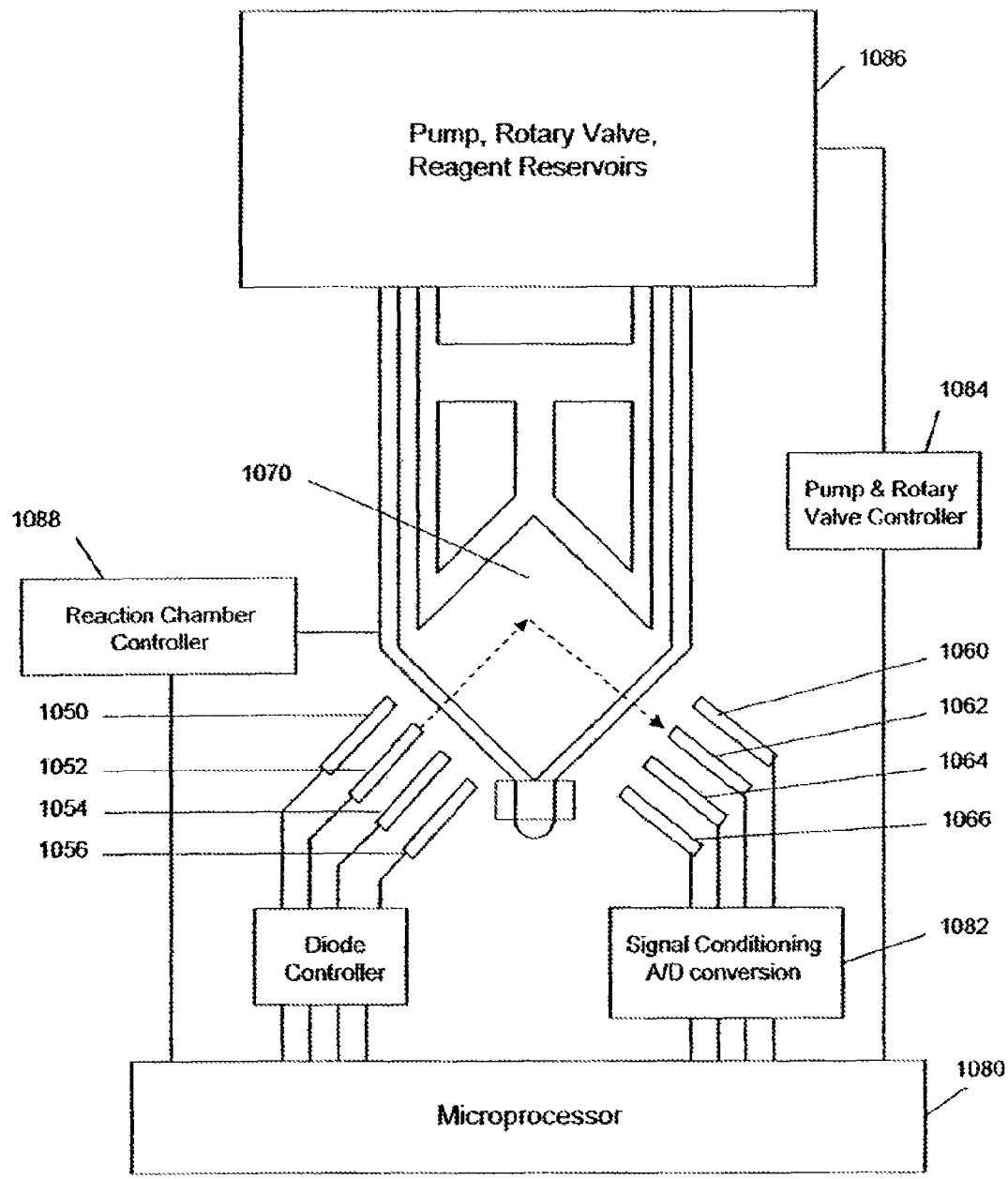
FIG. 1C is a diagram of an apparatus for implementing methods of the invention.

In one aspect of the invention, closed-loop control of initiation of a second-stage reaction is implemented by detecting an optical signal corresponding to a reaction parameter that reaches or exceeds a predetermined value. Preferably, the reaction parameter is concentration of an amplicon, usually the amplicon corresponding to a target polynucleotide. A variety of fluorescent signal generating schemes are available for producing a fluorescent signal in an amplification reaction that is monotonically related to amplicon concentration. such fluorescent signal generating schemes include, but are not limited to, molecular beacons, intercalating dyes, such as SYBR green, taqman probes, Amplifluor™ primers, "scorpion" primers, and the like, which are disclosed in references cited above. A variety of instrumentation systems may be employed to carry out such closed-loop control based on an optical signal generated by a reaction parameter, such as amplicon concentration. As described more fully below, in one aspect, a multichannel optical detection system disclosed by Christel et al., U.S. Pat. No. 6,369,893 is well-suited for such measurements. An schematic of such a system applicable to the present invention is illustrated in FIG. 1C. Christel et al. provide light-emitting diodes LEDs (1050) through (1056) for illuminating a reaction mixture in reaction chamber (1070). Fluorescence excited by LEDs (1050) through (1056) is collected by detectors (1060) through (1066), which typically are each operationally associated with a bandpass filter that restricts the wavelength of light that is detected. The excitation beams of LEDs (1050) through (1056) may be the same or different. In one aspect, bandpass filters are selected to selectively pass fluorescence emitted by a plurality of spectrally resolvable fluorescent dyes so that each detector (1060) through (1066) collects fluorescence primarily from only one of the plurality of fluorescent dyes. For use with the present invention, one of the LED-detector pairs, for example (1052) and (1062), is allocated to detecting the fluorescent signal from an amplicon corresponding to a target polynucleotide, and one of the LED-detector pairs, for example (1056) and (1066), is allocated to detecting fluorescent signal from an amplicon corresponding to a reference sequence.

Control of all components of the detection system and fluidly closed reaction system (1086) are controlled by microprocessor (1080). Optical signals collected by detectors (1060) through (1066) are processed by conventional optics and converted into electrical signals, which, after conventional pre-amplification and conditioning (1082), are digitized for storage and/or further processing by microprocessor (1080). In one aspect of the invention, microprocessor (1080) is programmed to continuously monitor the value of the signal collected by one of the detectors, such as detector (1062). When the value reaches or exceeds a pre-programmed level, then microprocessor (1080) initiates a subroutine that provides controllers (1084) with a series of commands to actuate components of fluidly closed reaction system (1086) to initiate a second-stage amplification reaction. Microprocessor (1080) also changes and/or regulates the temperature of reaction chamber (1070) through controller (1088). Temperature control is preferably achieved with one or more heating plates having resistive heating elements and a cooling fan as taught in Chang et. A1 U.S. Pat. No. 6,565,815 and U.S. Pat. No. 6,391,541 the disclosures of which are incorporated by reference herein. In embodiments employing closed-loop control, microprocessor (1080) may calculate values of characteristics of curves, such as (1013) or (1015) of FIG. 1B, at predetermined intervals so that they may be compared to a predetermined level. When such calculated value reaches or exceeds a predetermined level, then microprocessor (1080) initiates the subroutine to start a second-stage amplification reaction, as described above.

As mentioned above, a computer preferably performs steps of the method of initiating a second-stage reaction, as described above. In one embodiment, a computer comprises a processing unit, memory, I/O device, and associated address/data bus structures for communicating information therebetween. The processing unit may be a conventional microprocessor driven by an appropriate operating system, including RISC and CISC processors, a dedicated microprocessor using embedded firmware, or a customized digital signal processing circuit (DSP), which is dedicated to the specific processing tasks of the method. The memory may be within the microprocessor, i.e. level 1 cache, fast S-RAM, i.e. level 2 cache, D-RAM, or disk, either optical or magnetic. The I/O device may be any device capable of transmitting information between the computer and the user, e.g. a keyboard, mouse, network card, or the like. The address/data bus may be a PCI bus, NU bus, ISA, or any other like bus structure. When the computer performs the method of the invention, the above-described method steps may be embodied in a program stored in or on a computer-readable product. Such computer-readable product may also include programs for graphical user interfaces and programs to change settings on electrophoresis systems or data collection devices. In one aspect, the invention provides algorithms and computer-readable products for controlling the operations described in FIG. 1C in a selected fluidly closed reaction system.

In one aspect of the invention, a computer-readable product comprises a program for execution by a computer to control the performance of a nested amplification reaction in a fluidly closed reaction system. In one embodiment, such a program may comprise instructions for the following: (a) reading values of an optical signal from a first-stage amplification reaction, the optical signal being monotonically related to a concentration of an amplicon in the first-stage amplification reaction, and the values of the optical signal having a most recent value; (b) determining a baseline signal level from the values of the optical signal; (c) computing a predetermined level from the values of the optical signal; (d) comparing the predetermined value with the most recent value of the optical signal; (e) initiating a second-stage amplification reaction whenever the most recent value of the optical signal is equal to or greater than the predetermined level; and (f) repeating steps (d) and (e) until the second-stage reaction is initiated. As used herein, "a most recent value" in reference to an optical signal means the value corresponding to the most recent measurement of an optical signal by a detection system that is monitoring the amplification reaction. In other words, it is the most recent value of an amplicon growth curve as it is generated in the course of an amplification reaction.

In another aspect of the invention, a computer-readable product comprises a program for execution by a computer to control the performance of a nested amplification reaction in a fluidly closed reaction system. In one embodiment, such a program may comprise instructions for the following: (a) reading values of an optical signal from a first-stage amplification reaction, the optical signal being related to a quantity or concentration of an amplicon in the first-stage amplification reaction; (b) determining from the values of the optical signal if a threshold crossing has occurred; and (c) initiating a second-stage amplification reaction if and when the threshold crossing has occurred.

Nested PCRs are well-suited for use in the above apparatus, for example, where both first-stage and second-stage reactions are real-time PCRs. By way of example, a first-stage amplification reaction may be a real-time PCR in which an Amplifluor™ hairpin primer is used to generate a fluorescent signal whose intensity is monotonically related to an amplicon, e.g. Whitcombe et al., Nature Biotechnology, 17: 804-808 (1999). The second-stage amplification reaction may use the same or a different labeling scheme. Briefly, an Amplifluor™ hairpin primer has a target-binding portion, which is selected as with a conventional primer, and a hairpin portion at the 5' end of the target-binding portion, which maintains a fluorophore-quencher pair in close proximity whenever the hairpin is present, thereby quenching any fluorescent signal from the fluorophore. During the reverse extension step of the PCR, the duplex region of the hairpin is displaced as the reverse strand is extended through it to the end of the target polynucleotide, thereby moving the quencher away from the proximity of the fluorophore so that a fluorescent signal is generated. As the double stranded DNA product accumulates, the fluorescent signal from the reaction mixture increases. When the intensity of the fluorescent signal reaches or exceeds a predetermined level, e.g. 3 times baseline, the PCR is stopped and an effective portion of the reaction mixture is isolated, after which it is combined with second-stage reactants. By removing an effective portion of the first reaction mixture (and therefore a portion of the first amplicon) and treating it as a sample or specimen for amplification in a separate second reaction, interference from the first reaction components, such as fluorescence from the extended Amplifluor™ primers, may be substantially eliminated.

Nested NASBA reactions may also be implemented so that the second-stage NASBA is initiated after a signal generated related to a reaction parameter reaches or exceeds a predetermined level. A NASBA reaction is based on the simultaneous activity of a reverse transcriptase (usually avian myeloblastosis virus (AMV) reverse transcriptase), an RNase H, and an RNA polymerase (usually T7 RNA polymerase) with two oligonucleotide primers, which under conventional conditions can produce an amplification of a desired target sequence by a factor in the range of $10^9$ to $10^{12}$ in 90 to 120 minutes. In a NASBA reaction, nucleic acids are a template for the amplification reaction only if they are single stranded and contain a primer binding site. Because NASBA is isothermal (usually carried out at 41° C. with the above enzymes), specific amplification of single stranded RNA may be accomplished if denaturation of double stranded DNA is prevented in the sample preparation procedure. That is, it is possible to detect a single stranded RNA target in a double stranded DNA background without getting false positive results caused by complex genomic DNA, in contrast with other techniques, such as RT-PCR. By using fluorescent indicators compatible with the reaction, such as molecular beacons, NASBAs may be carried out with real-time detection of the amplicon. Molecular beacons are stem-and-loop-structured oligonucleotides with a fluorescent label at one end and a quencher at the other end, e.g. 5'-fluorescein and 3'-(4-(dimethylamino)phenyl)azo) benzoic acid (i.e., 3'-DABCYL), as disclosed by Tyagi and Kramer (cited above). An exemplary molecular beacon may have complementary stem strands of six nucleotides, e.g. 4 G's or C's and 2 A's or T's, and a target-specific loop of about 20 nucleotides, so that the molecular beacon can form a stable hybrid with a target sequence at reaction temperature, e.g. 41° C. A typical NASBA reaction mix is 80 mM Tris-HCl [pH 8.5], 24 mM $MgCl_2$, 140 mM KCl, 1.0 mM DTT, 2.0 mM of each dNTP, 4.0 mM each of ATP, UTP and CTP, 3.0 mM GTP, and 1.0 mM ITP in 30% DMSO. Primer concentration is 0.1 µM and molecular beacon concentration is 40 nM. Enzyme mix is 375 sorbitol, 2.1 µg BSA, 0.08 U RNase H, 32 U T7 RNA polymerase, and 6.4 U AMV reverse transcriptase. A reaction may comprise 5 µL sample, 10 µL NASBA reaction mix, and 5 µL enzyme mix, for a total reaction volume of 20 pt. Further guidance for carrying out real-time NASBA reactions is disclosed in the following references that are incorporated by reference: Polstra et al., BMC Infectious Diseases, 2: 18 (2002); Leone et al., Nucleic Acids Research, 26: 2150-2155 (1998); Gulliksen et al., Anal. Chem., 76: 9-14 (2004); Weusten et al., Nucleic Acids Research, 30(6) e26 (2002); Deiman et al., Mol. Biotechnol., 20: 163-179 (2002). Nested NASBA reactions are carried out similarly to nested PCRs; namely, the amplicon of a first NASBA reaction becomes the sample for a second NASBA reaction using a new set of primers, at least one of which binds to an interior location of the first amplicon.

As mentioned above, in one aspect, the invention provides methods of conducting reverse transcriptase reactions in series with one or more amplification reactions in a fluidly closed reaction system. In one embodiment, one or more RNA sequences, such a selected mRNAs extracted from a cell or tissue sample, may be amplified as follows: (i) transcribing one or more RNA sequences in a fluidly closed reaction system to form one or more complementary single stranded DNA sequences using reverse transcriptase reagents in a first reaction mixture; (ii) isolating a first effective portion of the first reaction mixture in the fluidly closed reaction system; and (iii) amplifying in the fluidly closed reaction system the one or more complementary single stranded DNA sequences in the first effective portion using first-stage amplification reagents in a second reaction mixture to form one or more first amplicons, the first-stage amplification reagents including initial primers for each of the complementary single stranded DNA sequences. The step of transcribing is carried out with a conventional reverse transcriptase reaction, components of which, i.e. reverse transcriptase reagents, are readily available commercially, e.g. Ambion. Roughly, in this embodiment, the reverse transcription reaction is treated similarly to a first-stage amplification reaction in a nested PCR, as described above. That is, an effective portion (a "first effective portion") of the reverse transcriptase reaction mixture is isolated, preferably by retaining such portion in a reaction chamber, while the remainder of the mixture is discarded. In this embodiment, such first effective portion means that the portion contains a sufficient quantity of complementary single stranded DNA that it may be detected by subsequent amplification reactions. Thus, the definitions for effective portion given above are applicable to a first effective portion in this embodiment. As mentioned above, the above two-stage reaction may be followed by a third stage nested amplification. This aspect of the method is conducted by the following additional steps: (i) isolating a second effective portion of said second reaction mixture in said fluidly closed reaction system; and (ii) amplifying in said fluidly closed reaction system said one or more first amplicons in said second effective portion using second-stage amplification reagents in a third reaction mixture to form one or more second amplicons, the second-stage amplification reagents including at least one secondary primer for each of the one or more first amplicons, such that each secondary primer is nested in such first amplicon relative to said initial primer of such first amplicon. Preferably, the above aspect of the invention is performed as an RT-nPCR in a fluidly closed reaction system.

Systems for Implementing Methods of the Invention

Methods of the invention may be implemented by a variety of systems and apparatus that are based on different engineering approaches for sequestering reagents, moving reagents and reaction products into and out of reactions, controlling temperature, and detecting reaction products. Selection of a system depends on many factors including, but not limited to, availability of samples or specimens, form of samples or specimens, degree of hazard or infectivity posed by samples or specimens, desirability of portability, nature of the amplification reaction employed, and the like. Exemplary systems that may be used to implement methods of the invention include fluidly closed reaction systems employing a rotary valve and a piston-type fluid pump under microprocessor control, such as disclosed in Christel et al., U.S. Pat. No. 6,369,893 and Dority, U.S. Pat. No. 6,374,684; closed disposable cuvettes having flexible reagent reservoirs for mechanically driving samples, reactants and products through reaction chambers and detection stations, as disclosed in Schnipelsky et al., U.S. Pat. No. 5,229,297; and Findlay et al., Clin. Chem., 39: 1927-1933 (1993); and microfluidics devices, such as disclosed in the references cited under Definitions, and further disclosed in Shoji et al., Appl. Biochem. Biotechnol., 41: 21-34 (1993) and J. Micromech. Microeng., 4: 157-171 (1994); McCormick et al., Anal. Chem., 69: 2626-2630 (1997); Cheng et al., Topics Curr. Chem., 194: 215-231 (1998); Stave et al., U.S. Pat. No. 6,663,833; Neri et al., U.S. Pat. No. 5,714,380; Northrup et al., U.S. Pat. No. 5,589,136; and the like. Such systems are capable of fluidly transferring reactants, samples, and reaction products between reservoirs and reaction chambers in a controlled manner. That is, such systems move reactants, samples, reaction products, and the like, in liquid solutions under liquid-moving force in a directed manner. Liquid-moving forces include differential pressure generated by various kinds of pumps or compressed gas reservoirs, electrokinetic pumps, and the like.

In one aspect, methods of the invention may be conveniently implemented by specific designs and methods of operation of rotary valves, reactant and waste reservoirs, and reaction chambers generally disclosed in Dority (cited above). In another aspect, in which real-time monitoring of amplification products is desired, such apparatus is conveniently used with the temperature controller and fluorometer disclosed by Christel et al. (cited above). As will be described more fully below, the apparatus of Christel et al. may further be used to provide closed-loop control of the initiation of a second-stage reaction in the fluidly closed reaction system of Dority.

FIGS. 2A-2I show diagrammatically operation of an apparatus that follows the general design approach disclosed in Dority (cited above), which permits partial evacuation of a reaction chamber to leave an effective portion of a first reaction mixture in the reaction chamber to serve as a sample for a second amplification reaction. The partial evacuation is effected by controlling electronically the volume displaced by a piston-type pump. Alternatively, as described below, partial evacuation of the reaction chamber may also be carried out passively by an alternative design of the reaction chamber wherein a "dead volume" in the chamber defines an effective portion and permits full strokes of a piston-type pump to be employed.

Figure 2A:
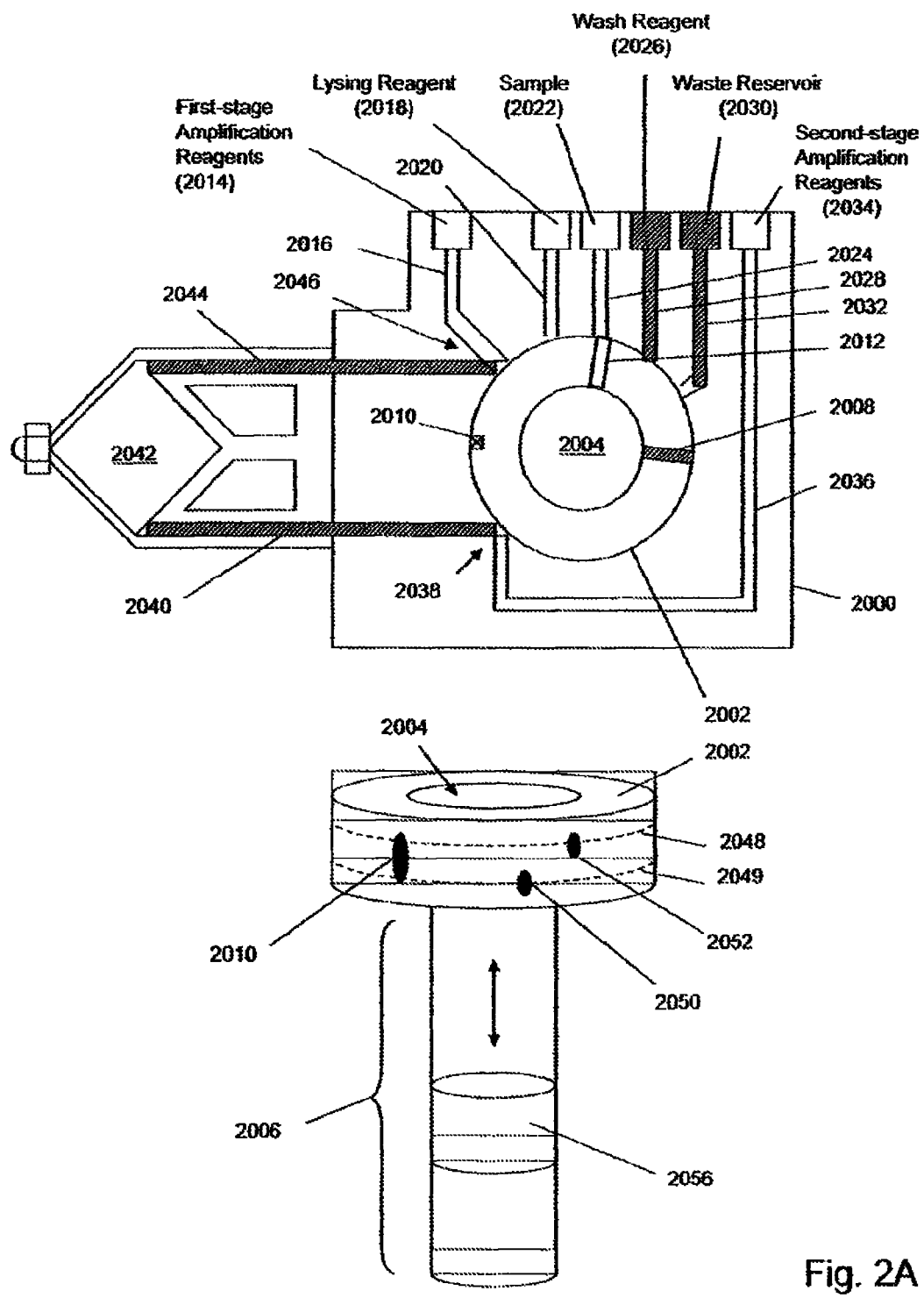
FIGS. 2A-2H diagrammatically illustrate implementation of a nested amplification reaction in a fluidly closed reaction systems that employs a rotary valve and a piston-type fluid pump.

FIG. 2A shows housing (2000) that contains rotary valve (2002) having internal chamber (2004) that is operationally connected to piston-type pump (2006). Up-strokes of piston (2056) of pump (2006) pressurize chamber (2004) and force fluid contents out through whatever ports that may be in communication with reservoirs or the like; likewise, down strokes of piston (2056) of pump (2006) depressurize chamber (2004) and draw fluids in through whatever ports may be open and in communication with reservoirs or the like. Further descriptions of the operation and construction of such pump-rotary valve devices and the use of chamber (2004) for sample preparation is provided by Dority (cited above), which is incorporated by reference for this purpose. Rotary valve (2002) has various ports, for example (2050) and (2052), and associated passages, (2008) and (2012), that permit chamber (2004) to be in fluid communication with various reservoirs (described more fully below) or reaction chamber (2042) whenever such ports are aligned with corresponding ports to passages to such reservoirs or reaction chamber (2042). In the present exemplary embodiments, the longitudinal axes of such associated passages are radially disposed in rotary valve (2002) within either one of two planes perpendicular to the axis of rotary valve (2002) (shown with dashed lines (2048) and (2049)), such that chamber (2004) may be placed in fluid communication with ports of passages to reservoirs, and the like, disposed in housing (2000). Rotary valve (2002) further includes connecting passages (2010), which permit a port in one plane of the valve to be placed in fluid communication with ports of housing (2000) that are aligned with the other plane of rotary valve (2002). Such connection passages (2010) do not permit fluid communication with interior chamber (2004). As illustrated in FIG. 2A, when such connecting passages (2020) are aligned at (2046) with ports of passages (2044) and (2016), passages (2044) and (2016) are in fluid communication. Likewise, when such connecting passages (2020) are aligned at (2038) with ports of passages (2040) and (2036), passages (2040) and (2036) are in fluid communication. In both FIGS. 2A-2I and 3A-3I, cross-hatched passages and reservoirs in housing (2000) are in the pump-proximal plane of rotary valve (2002), whereas the non-hatched passages and reservoirs are in the pump-distal plane. As mentioned above, rotary valve (2002) may place interior chamber (2004) in fluid communication with various reservoirs and reaction chamber (2042) that are connected by passages and have ports in the seat of housing (2000) that rotary valve (2002) rotates within. In the present example, such reservoirs include the following; (i) reservoir (2014) containing first-stage amplification reagents, which may be fluidly connected to rotary valve (2002) by passage (2016); (ii) reservoir (2018) containing lysing reagents, for example, for disrupting surface membranes of cellular samples, which reservoir may be fluidly connected to rotary valve (2002) by passage (2020); (iii) reservoir (2022) containing sample or specimen material, which may be fluidly connected to rotary valve (2002) by passage (2024); (iv) reservoir (2026) containing wash reagent, which may be fluidly connected to rotary valve (2002) by passage (2028); (v) waste reservoir (2030), which may be fluidly connected to rotary valve (2002) by passage (2032); and (vi) reservoir (2034) containing second-stage amplification reagents, which may be fluidly connected to rotary valve (2002) by passage (2036).

Figure 2B:
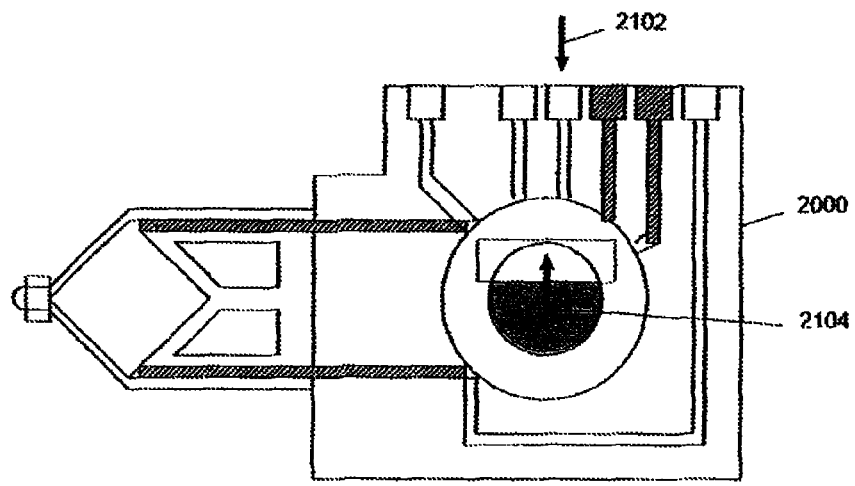
Figure 2B:
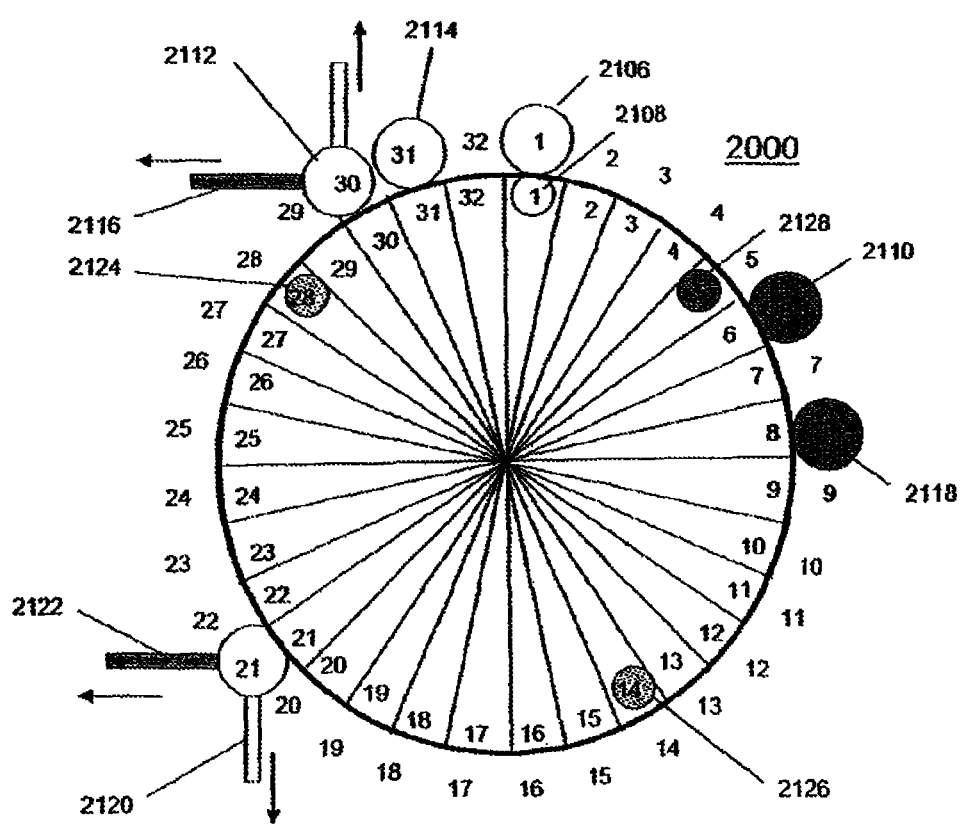
Figure 2C:
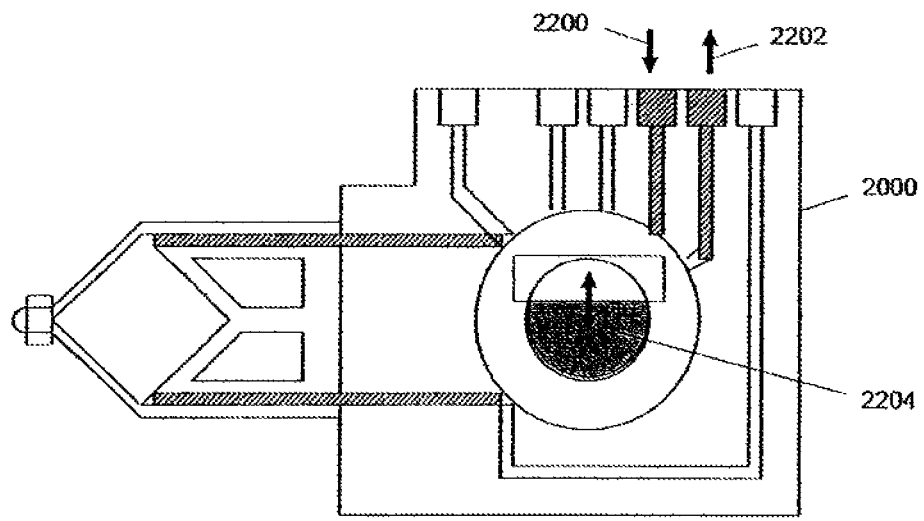
Figure 2C:
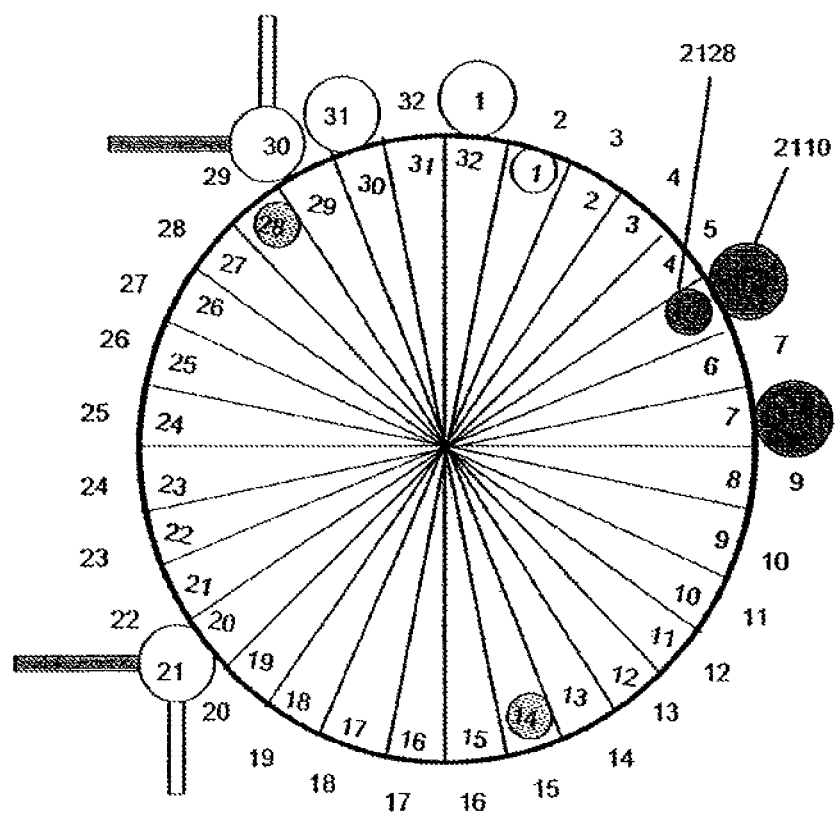
Figure 2D:
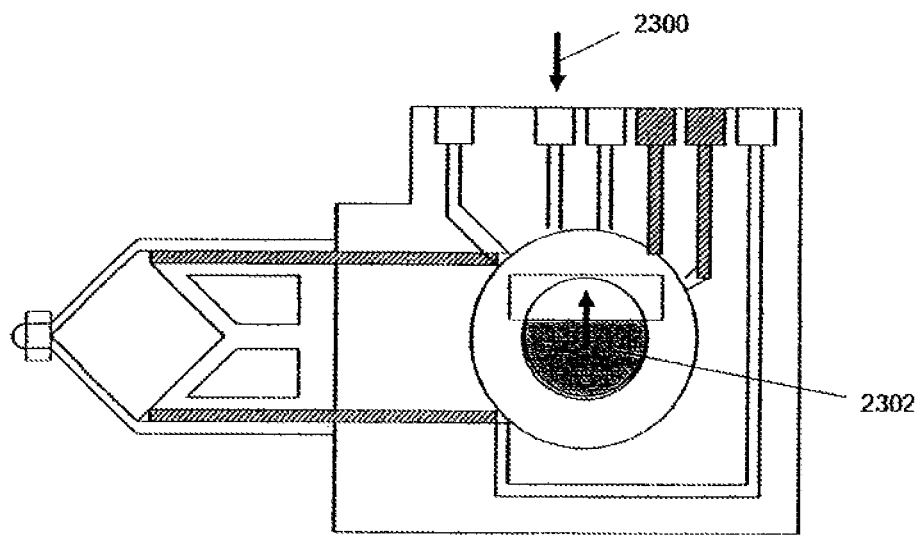
Figure 2D:
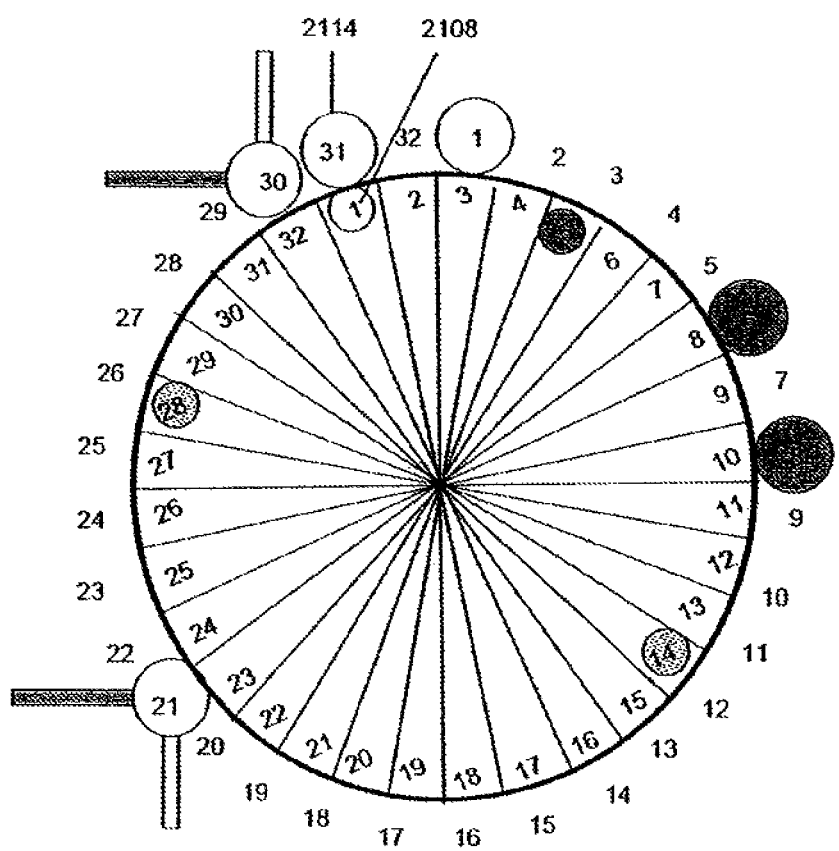
Figure 2E:
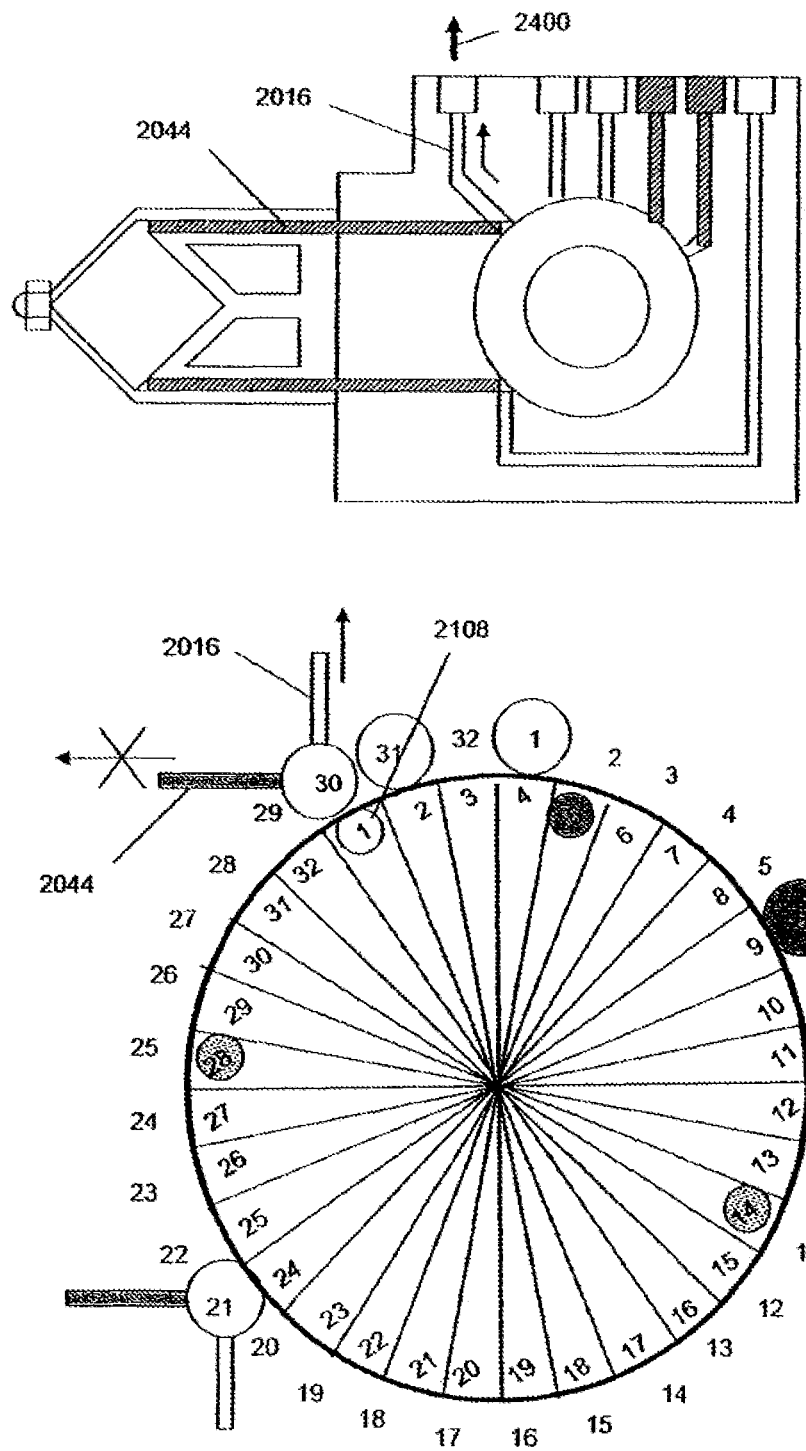

FIGS. 2B to 2H illustrate the operation of the apparatus of FIG. 2A for carrying out a two-staged amplification reaction under fluidly closed conditions. For the purpose of teaching how particular embodiments of rotary valve (2002) operate, rotary valve (2002) is shown diagrammatically in each of FIGS. 2B to 2H divided into 32 sectors, which are numbered. Adjacent to each numbered sector of rotary valve (2002) there is a corresponding location in the seat of housing (2000) that is also numbered. The number 32 is merely a design choice that reflects, among other things, the capacity of rotary valve (2002) to provide interconnections in a complex system of reservoirs and chambers. At a starting position of rotary valve (2002), the numbers adjacent to each other at each sector for the two sets is the same, as shown in FIG. 2B. Certain of the numbers ("inner numbers") on rotary valve (2002) are circled (1, 5, 14, 28), and certain of the numbers ("outer numbers") adjacent and exterior to rotary valve (2002) are circled (1, 6, 8, 21, 30, 31). The circles indicate the sectors at which the ports to the various reservoirs and chambers are located. Circles with shaded interiors, e.g. 5, 6, and 8, indicate ports located in the "pump-proximal" plane (2049) of rotary valve (2002) and un-shaded circles, e.g. 1, 21, 30, 31, indicate ports located in the "pump-distal" plane (2048) of rotary valve (2002). Circles (2126) and (2124) at sectors 14 and 28, respectively, that have stippled interiors indicate connecting passages (2010). In FIG. 2B, rotary valve (2002) is shown at a starting position in which port 1 (2108) of the valve is aligned with port 1 of housing (2000) so that sample reservoir (2022) is in fluid communication with interior chamber (2004) where sample preparation procedures may be carried out. With a down-stroke of pump (2006), sample is drawn through the path defined by passage (2024), ports (2106) and (2108), and passage (2012) to fill (2104) interior chamber (2104). Wash steps may be performed as shown in FIGS. 2C and 2D. Briefly, in FIG. 2C, rotary valve (2002) is rotated so that port (2128) in sector 5 aligns with port 6 (2110) of housing (2000) so that with an down-stroke of piston (2056) wash solution in reservoir (2026) is drawn (2200) (and (2204)) into interior chamber (2004). By rotating rotary valve (2002) so that port 5 (2128) aligns with port 8 of housing (2000) permitting fluid communication between interior chamber (2004) and waste reservoir (2030), wash solution in interior chamber (2004) may be expelled (2202) into waste reservoir (2030) upon an up-stroke of piston (2056). This process may be repeated as needed.

Figure 2F:
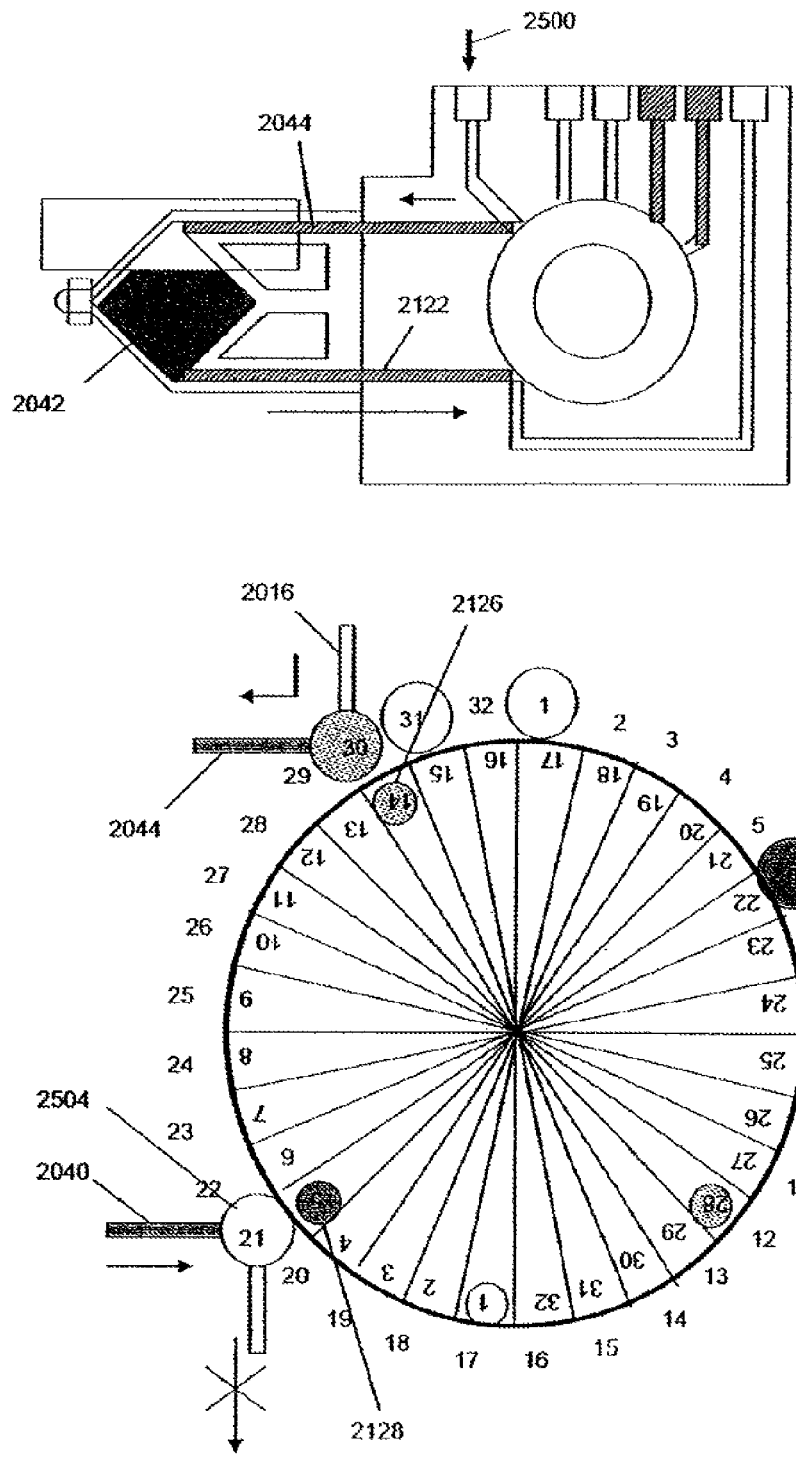
Figure 2G:
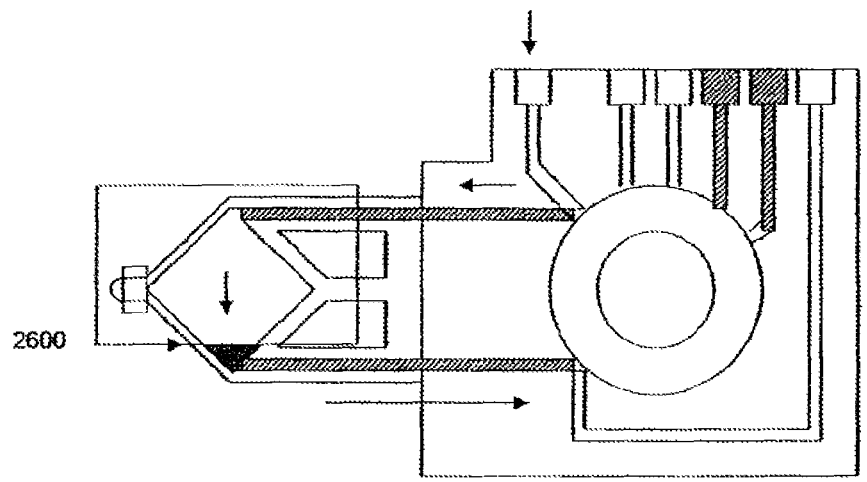
Figure 2G:
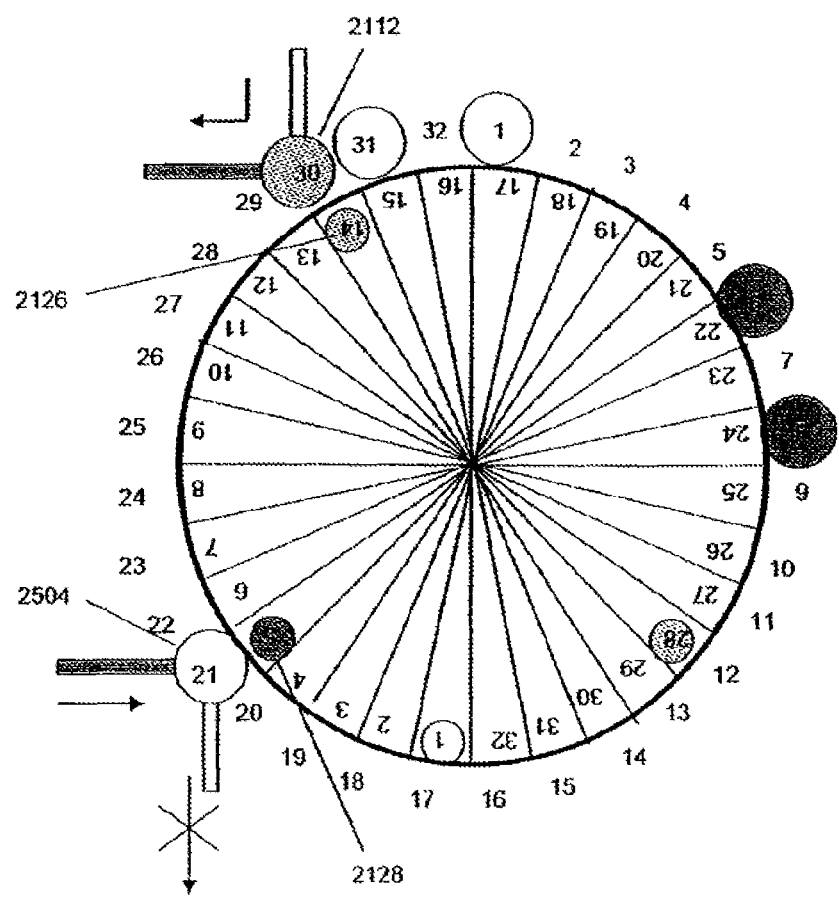

For samples containing intact cells, a reagent for lysing cell surface membranes may be added to interior chamber (2004) to generate a lysate, which may be washed further as needed. In FIG. 2D, rotary valve (2002) is rotated to align port 1 (2108) of the valve with port 31 (2114) of housing (2000), thereby putting interior chamber (2004) in fluid communication with reservoir (2018). A down-stroke of piston (2056) will drawn (2300) lysing reagent from reservoir (2018) into interior chamber (2302). After incubation in the lysing reagent, the sample may optionally be washed additionally as described above. After incubation, or incubation and further washing, rotary valve (2002) is rotated so that port 1 (2108) is aligned with the port of passage (2016) (at sector 30) of housing (2000), so that the lysate in interior chamber (2004) is forced (2400) by an up-stroke of piston (2056) through ports 1 and 30, passage 2016, and into reservoir (2014) where it mixes with first-stage amplification reagents. There is no flow into passage (2044) because there is no fluid connection between ports 1 and the port of passage (2044), as one is in the pump-proximal plane (2049 in FIG. 2A) and the other is in the pump-distal plane (2048 in FIG. 2A) of rotary valve (2002). After mixing the sample material and first-stage amplification reagents, the mixture is transferred to reaction chamber (2042). As shown in FIG. 2F, this may be accomplished by rotating rotary valve (2002) so that port 5 (2128) aligns with port of passage (2040) that is in fluid communication with reaction chamber (2042) and connecting passage 14 (2126) is aligned with the ports of passages (2016) and (2044) at sector 30 (2112). With a down-stroke of piston (2056), reaction mixture is drawn (2500) from reservoir (2014) through passage (2016), connecting passage 14, and passage (2044) into reaction chamber (2042), where a first-stage amplification reaction is conducted, such as a real-time PCR using monitoring optics as taught by Christel et al. (cited above). According to another embodiment, the first stage amplification reagents are simply placed in the reaction chamber (2042) so that the first reactant reservoir (2014) is not required, and the sample material is fluidly transferred to the reaction chamber where it mixes with the first stage amplification reagents to from the first reaction mixture.

Figure 2H:
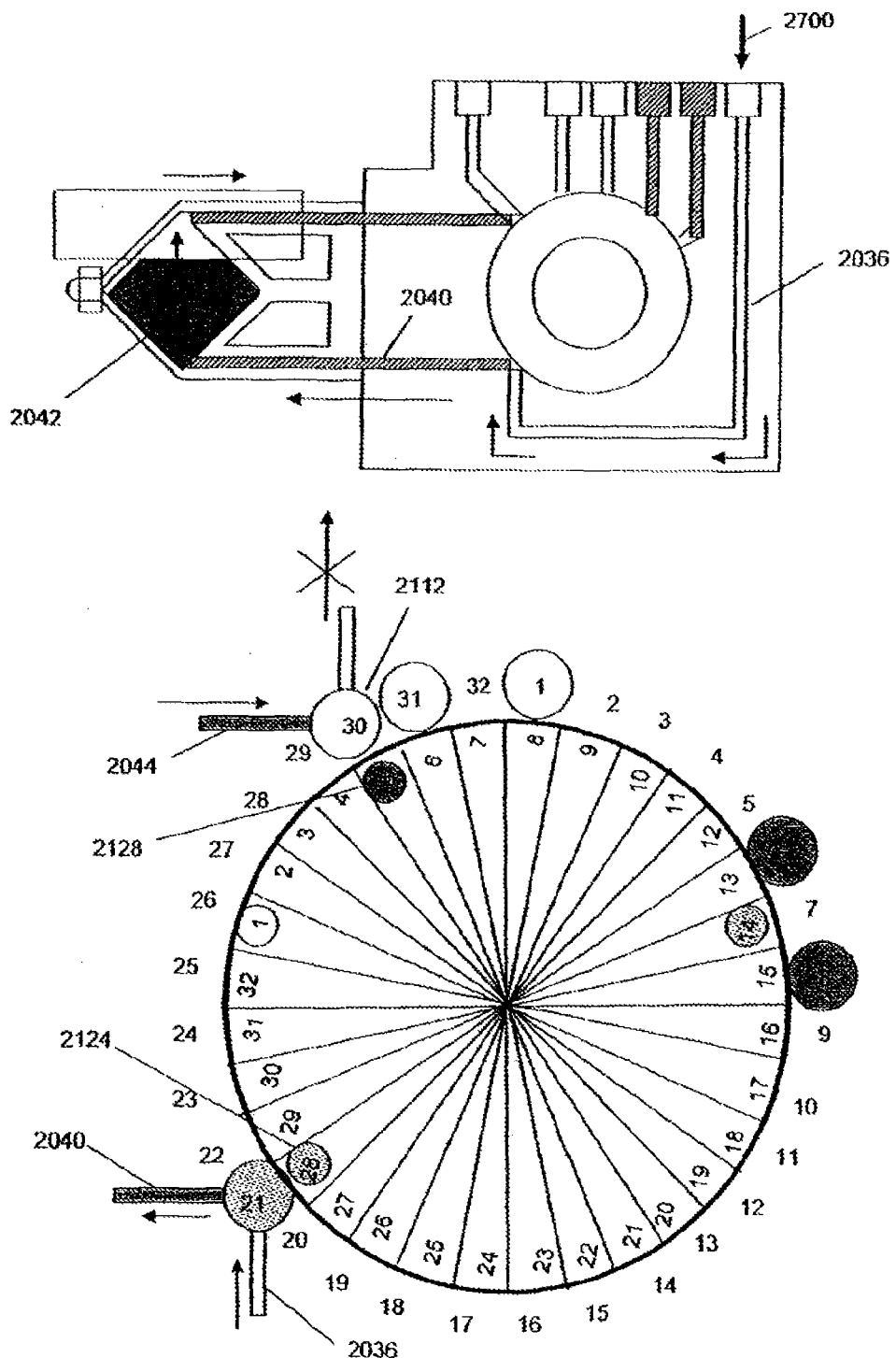

The first stage amplification reaction is carried out in the reaction chamber to produce a first amplicon. After the first-stage amplification reaction is halted and (optionally) piston (2056) has been brought proximal to rotary valve (2002) by exhausting into waste reservoir (2030), the bulk of the reaction mixture may be removed from chamber (2042) with a partial down-stroke of piston (2056), wherein the amount of reaction mixture left (2600) in reaction chamber (2042) is predetermined by carrying out the down-stroke of piston (2056) under computer control. The amount left is selected to be effective for carrying out the next stage of the multi-stage reaction; thus, the actual volume in particular embodiment may require routine experimentation to determine. After such partial removal, as shown in FIG. 2H, rotary valve (2002) is rotated so that port 5 (2128) is align with the port of passage (2044) and so that connecting passage is align at sector 21 (2504) with the ports of passage (2040) and (2036). With this configuration, there is fluid communication between reservoir (2034) containing second-stage amplification reagents and interior chamber (2004) along the following path: passage (2036), connecting passage 28 (2124), passage (2040), reaction chamber (2042), and passage (2044). With a downstroke of piston (2056), second-stage amplification reagents are drawn (2700) from reservoir (2034) and into reaction chamber (2042), where a second-stage amplification is conducted, with the amplicon in the effective portion (2600) serving as a sample.

Figure 3A:
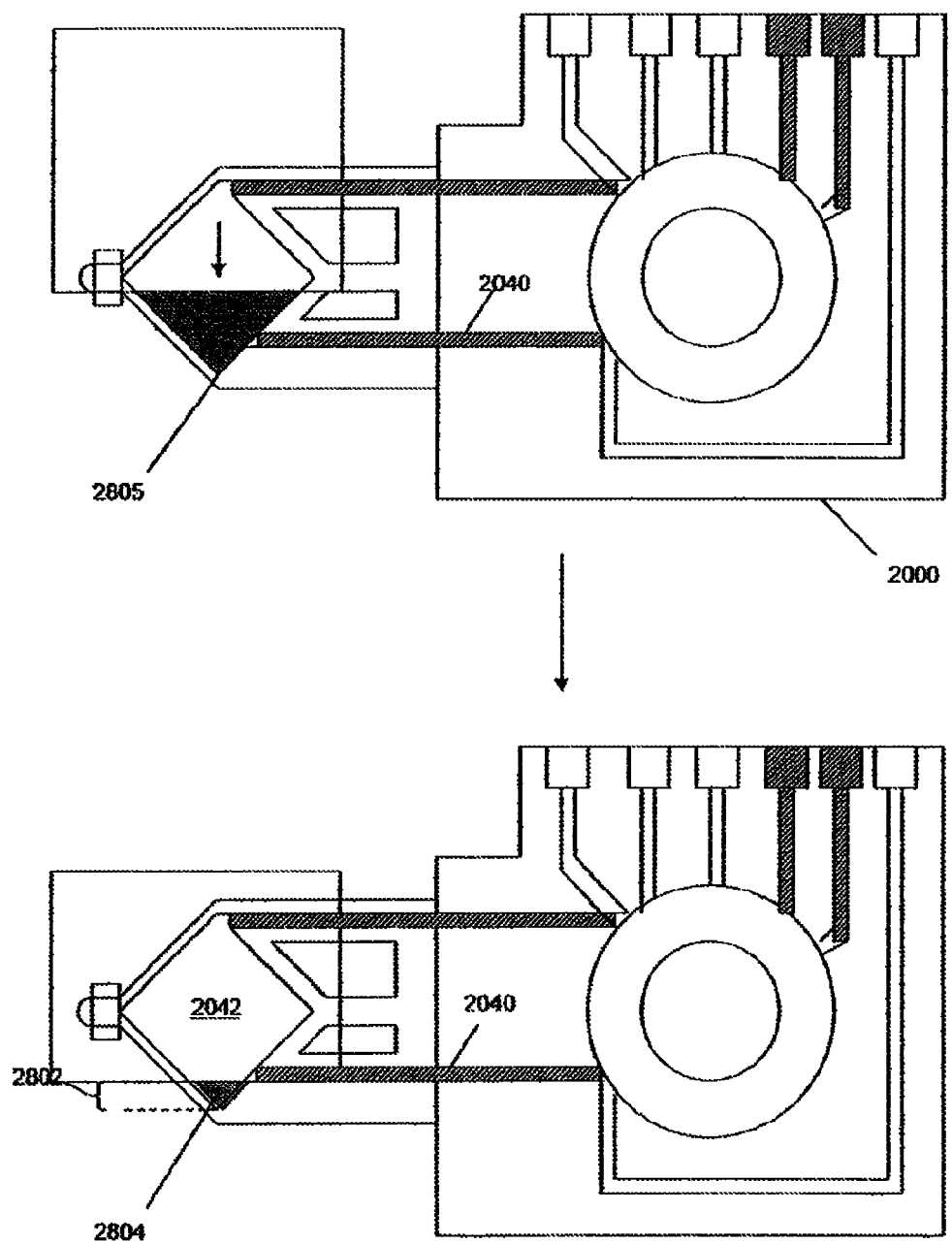
FIGS. 3A-3C diagrammatically illustrate alternative reaction chambers for implementing certain embodiments of the invention.
Figure 3B:
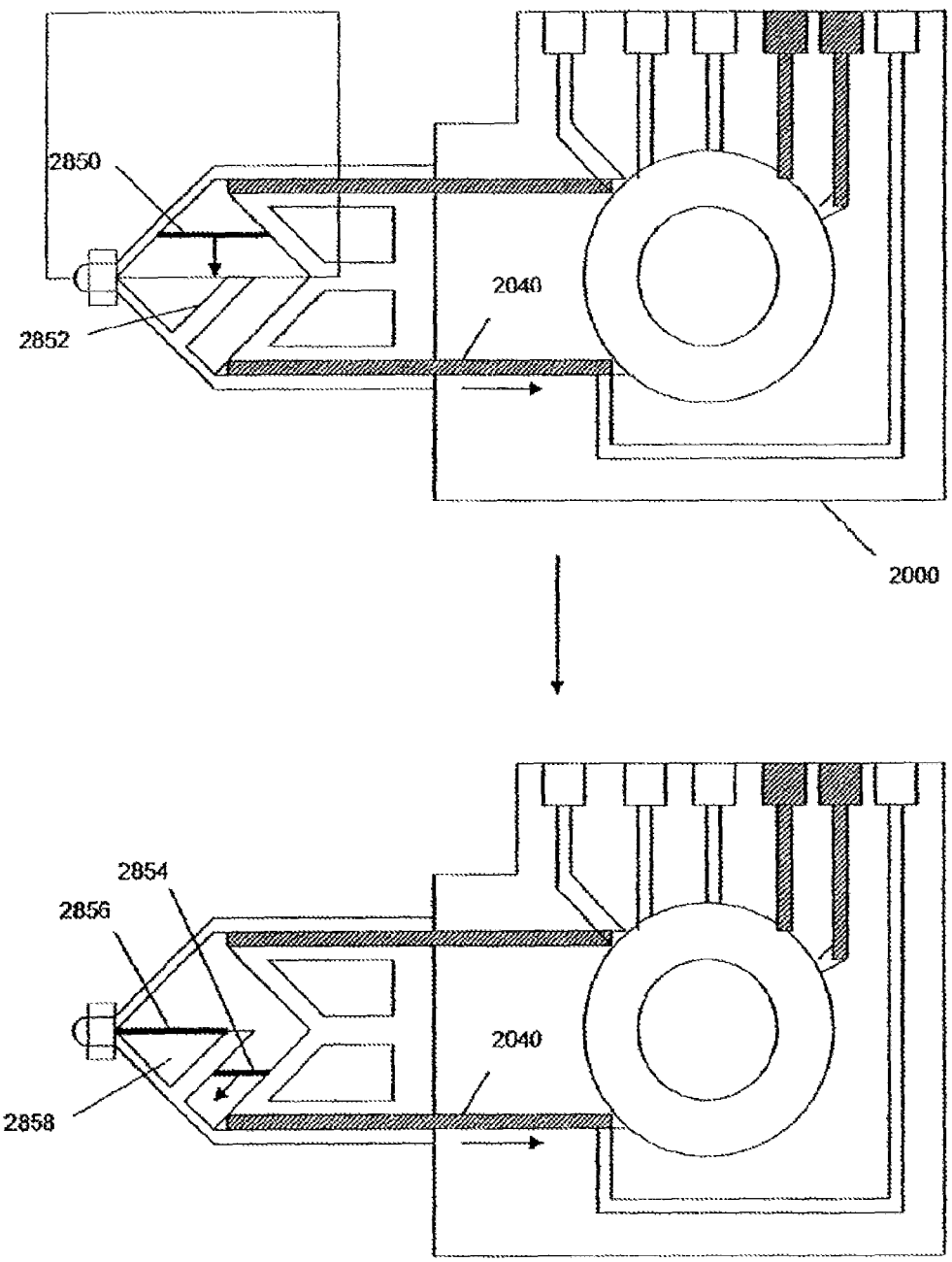

As illustrated in FIG. 3A, as an alternative to using a partial pump stroke to determine the volume of reaction mixture that is retained in reaction chamber (2042) for the second-stage amplification (and therefore the effective portion), the volume may be controlled passively by employing a reaction chamber (2042) that contains a "dead volume" of predetermined size. This may be accomplished by moving the reaction chamber port of passage (2040) "higher" along the wall of reaction chamber (2042) so that a portion (2804) of a reaction mixture remains in chamber (2042) at the bottom (2805) of reaction chamber (2042) whenever it is drained through passage (2040). Such passive control is especially desirable in applications where reliability is required and there is low tolerance for break downs due to electrical component or software failures. In one aspect, the invention provides reaction chambers (2042) that have a dead volume for collecting an effective portion of a reaction mixture to serve as a sample for a second-stage amplification reaction. Alternatively, instead of altering the design of passage (2040), a retaining member such as a retaining wall (2852) may be added to the reaction chamber, as shown in FIG. 3B. In this embodiment, as fluid level (2850) is lowered by drainage of a reaction mixture through passage (2040), a volume (2858) is retained (referred to herein as a "retained volume") in the reaction chamber. Fluid not retained by retaining member (2852) is fluidly transferred out of the reaction chamber to the waste chamber through passage (2040) until substantially no fluid remains in the chamber, except that retained by retaining member (2852).

Figure 3C:
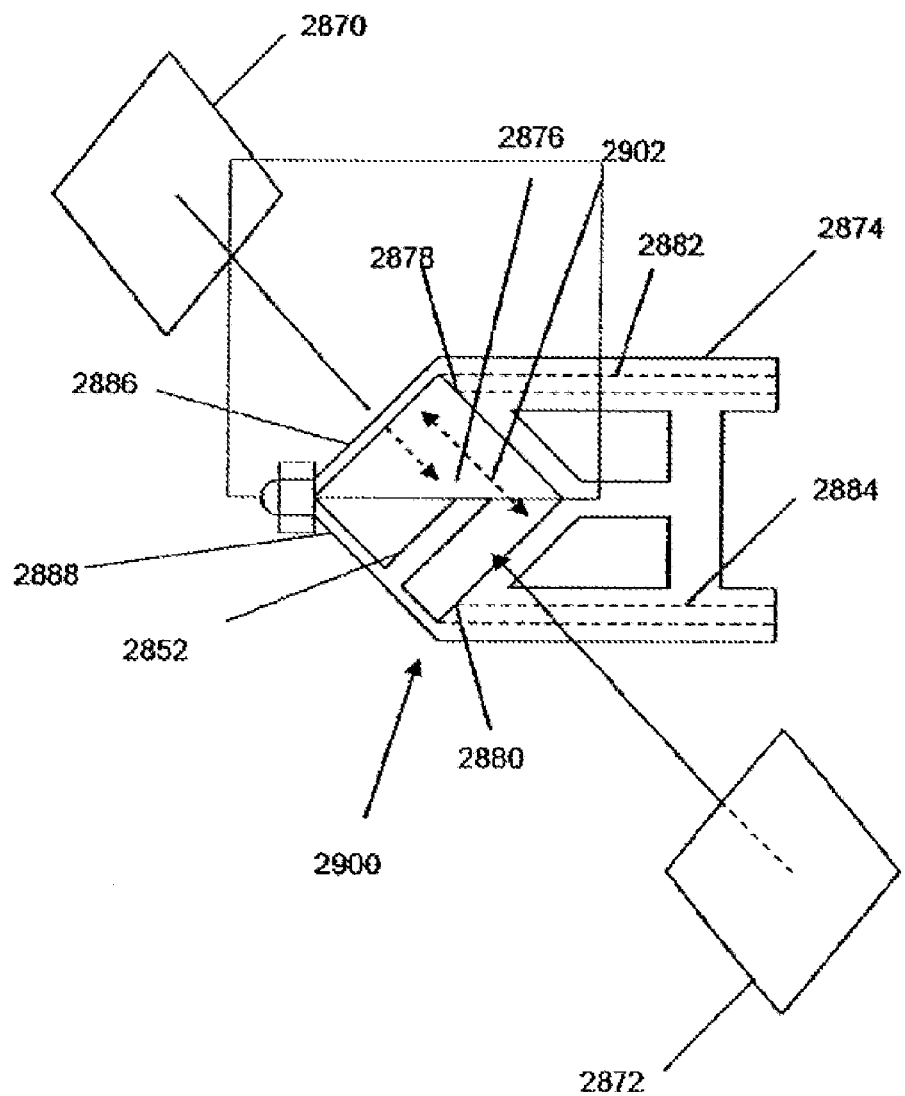

In one aspect of the invention, a reaction vessel is provided for use with apparatus and methods of the invention. FIG. 3C diagrammatically illustrates one embodiment of such a reaction vessel. Most generally, reaction vessel (2874) comprises reaction chamber (2876) for containing a liquid, such as a reaction mixture, an inlet port (2878) connected to reaction chamber (2876) by inlet channel (2882), an outlet port (2880) connected to reaction chamber (2876) by outlet channel (2884), and a retaining member (2852) in reaction chamber (2876) positioned so as to retain a volume of liquid (e.g. (2858) of FIG. 3B) whenever reaction chamber (2876) is drained of liquid through outlet port (2880) and outlet passage (2884). In one embodiment, reaction vessel (2874) comprises rigid frame (2900) that defines side walls of reaction chamber (2876), including side walls (2886) and (2888) that are each optically transmissive and angularly offset from each other, thereby permitting illumination of fluorescent indicators in reaction chamber (2876) and collection of fluorescent signals generated thereby. In a preferred embodiment described more fully above, fluorescent indicators in reaction chamber (2876) are illuminated through one of side walls (2886) or (2888) and fluorescent signals are collected through the other side wall (2886) or (2888). A fluid-tight reaction chamber (2876) is formed from rigid frame (2900) by sealingly attaching to opposite sides of such frame first and second plastic films (2870) and (2872), respectively. When thus attached, first and second plastic films (2870) and (2872) form first and second major walls, respectively, of reaction chamber (2876). Preferably, plastic films (2870) and (2872) are sufficiently flexible to conform to a thermal surface to permit efficient heat conduction for precise regulation of temperature inside chamber (2876). Reaction chamber (2876) has a depth (the dimension going into the plane of the drawing in FIG. 3C) and a width (2902), wherein in the embodiments illustrated width (2902) is a measure of the surface areas of the major walls of reaction chamber (2876). In one aspect of the reaction vessel, width (2902) and reaction chamber (2876) depth are selected so that there is a large surface-to-volume ratio for rapid heating or cooling of contents of reaction chamber (2876). In one embodiment, width (2902) and depth of reaction chamber (2876) has a ratio of approximately 4:1 and the depth of reaction chamber (2902) is less than 2 mm.

Internal Standards

Often times it is desirable to compare readouts from different assays, for example, when attempting to determine whether measured expression levels of a target gene in a patient specimen are within normal ranges. In medical applications in particular, it is often desired to compare assay results from a patient sample to those of reference samples. Such comparisons are readily made by determining ratios of a signal associated with the target polynucleotide to a signal associated with a reference sequence from the same sample. This permits values for a target polynucleotide to be compared to those from other samples or specimens. Use and selection of internal standards, and in particular, reference sequences, are well-known to those of ordinary skill in the art, as reflected in the following references that are incorporated by reference: Radonic et al., Biochem. Biophys. Res. Comm., 313: 856-862 (2004); Bustin, J. Mol. Endoccrinol., 29: 23-39 (2002); Hoorfar et al., J. Clin. Microbiol., 42: 1863-1868 (2004); and the like. It is understood that the signal or a value associated with a reference sequence may also be a function, for example, an average, of signals or values measured from multiple reference sequences.

In one aspect of the invention, such relative values of target polynucleotides is provided by amplifying both reference sequences and target polynucleotides in a first-stage amplification reaction, amplifying only amplicons of target polynucleotides in a second-stage amplification reaction, and forming a ratios each comprising a signal from an amplicon of a target polynucleotide in the second amplification reaction to a signal from an amplicon of a reference sequence in the first amplification reaction. This aspect of the invention is particularly well-suited for comparing levels of rare, or very low level, target polynucleotides from different samples. In such circumstances, reference sequences are typically present in great excess of the target polynucleotides; consequently, if both sequences were to undergo two stages of amplification, the reference sequence signal may easily overwhelm the target polynucleotide signal, if the respective signals even slightly overlap, as is the case with emission bands of organic fluorescent dyes. Accordingly, in one embodiment of this aspect, a method of measuring relative quantities of a target polynucleotide in multiple samples is provided by carrying out a nested PCR wherein (i) a reference sequence is amplified in a first-stage PCR but not in a second-stage PCR and (ii) relative quantities of a target polynucleotide are determined from ratios of the following two measurements: a fluorescent signal from an amplicon produced in the second-stage PCR from a target polynucleotide, and a fluorescent signal from an amplicon produced in the first-stage PCR from a reference sequence. In a preferred embodiment, both the first-stage and second-stage reactions are real-time PCRs. In another embodiment of this aspect, a method of measuring relative quantities of a target polynucleotide in multiple samples is provided by carrying out a nested NASBA reaction wherein (i) a reference sequence is amplified in a first-stage NASBA reaction but not in a second-stage NASBA reaction and (ii) relative quantities of a target polynucleotide are determined from ratios of the following two measurements: a fluorescent signal from an amplicon produced in the second-stage NASBA reaction from a target polynucleotide, and a fluorescent signal from an amplicon produced in the first-stage NASBA reaction from a reference sequence. In a preferred embodiment, both the first-stage and second-stage reactions are real-time NASBA reactions. In both of the approaches described above, the second stage reactions may be initiated by monitoring an optical signal in the first-stage PCR or NASBA. In one aspect, such optical signal provides a measure of the amount of amplicon of either the reference sequence or target polynucleotide or both. In one aspect, the second-stage reaction may be initiated when the optical signal reaches or exceeds a predetermined level that is in the range of from 1.5 to 10 times a baseline signal level. In another aspect, the second-stage reaction may be initiated when the optical signal reaches or exceeds a predetermined level that corresponds to a root of the second derivative of an amplicon growth curve corresponding to a reference sequence.

The type of internal standard or reference sequence selected depend on the nature of the samples being analyzed. For samples comprising mammalian cells or tissues exemplary references sequences are listed in Table I.

TABLE I

Exemplary Reference Sequences

| Reference Gene | Gene Product Name | NCBI Accession No. |
|---|---|---|
| GAPDH | glyceraldehydes 3-phosphate dehydrogenase | J02642 |
| G6PDH | glucose 6-phosphate dehydrogenase | X03674 |
| HPRT | hypoxanthine-guanine phosphoribosyltransferase | L29382 |
| PBGD | porphobilinogen deaminase | X04808 |
| Alb | | L00132 |
| Act | β-actin | M10277 |
| Tub | α-tubulin | X01703 |
| TBP | TATA-box binding protein | M55654 |
| L13 | ribosomal protein L13 | X56923 |
| β2M | β2-microglobulin | J00115 |
| PPIA | peptidyl prolyl isomerase A | Y00052 |
| PLA | phospholipase A2 18S and 28S ribosomal RNA | M86400 |

Sample or Specimen Preparation

Samples or specimens containing target polynucleotides may come from a wide variety of sources for use with the present invention, including cell cultures, animal or plant tissues, patient biopsies, environmental samples, or the like. Samples are prepared for assays of the invention using conventional techniques, which typically depend on the source from which a sample or specimen is taken.

Samples or specimens are collected so as to minimize the chance of contamination of the sample or specimen by external elements, or the environment by the sample or specimen if it contains hazardous components. Generally, this is carried out by introducing a sample for analysis, e.g., tissue, blood, saliva, etc., directly into a sample collection chamber within a fluidly closed system. Typically, the prevention of cross-contamination of the sample may be accomplished by directly injecting the sample into the sample collection chamber through a sealable opening, e.g., an injection valve, or a septum. Generally, sealable valves are preferred to reduce any potential threat of leakage during or after sample injection. In addition to the foregoing, the sample collection portion of the device may also include reagents and/or treatments for neutralization of infectious agents, stabilization of the specimen or sample, pH adjustments, and the like. Stabilization and pH adjustment treatments may include, e.g., introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

Prior to carrying out amplification reactions on a sample, it will often be desirable to perform one or more sample preparation operations upon the sample. Typically, these sample preparation operations will include such manipulations as extraction of intracellular material, e.g., nucleic acids from whole cell samples, viruses and the like. One or more of these various operations may be readily incorporated into the fluidly closed systems contemplated by the present invention.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like. Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Physical methods may be used to extract the nucleic acids and denature DNA binding proteins. Wilding et al., U.S. Pat. No. 5,304,487, incorporated herein by reference in its entirety for all purposes, discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to perform cell lysis/extraction, including, e.g., subjecting cells to ultrasonic agitation, or forcing cells through small apertures, thereby subjecting the cells to high shear stress resulting in rupture.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like, i.e., poly-T oligonucleotides for mRNA purification. Alternatively, desalting methods may generally take advantage of the high electrophoretic mobility and negative charge of DNA compared to other elements. Electrophoretic methods may also be utilized in the purification of nucleic acids from other cell contaminants and debris. In one example, a separation channel or chamber of the device is fluidly connected to two separate "field" channels or chambers having electrodes, e.g., platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g., acting as a salt junction). Such barriers may include, e.g., dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use. In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

For a number of applications, it may be desirable to extract and separate messenger RNA from cells, cellular debris, and other contaminants. As such, a system of the present invention may, in some cases, include an mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself.

In some applications, such as measuring target polynucleotides in rare metastatic cells from a patient's blood, an enrichment step may be carried out prior to conducting an assay, such as by immunomagnetic isolation. Such isolation or enrichment may be carried out using a variety of techniques and materials known in the art, as disclosed in the following representative references that are incorporated by reference: Terstappen et al., U.S. Pat. No. 6,365,362; Terstappen et al., U.S. Pat. No. 5,646,001; Rohr et al., U.S. Pat. No. 5,998,224; Kausch et al., U.S. Pat. No. 5,665,582; Kresse et al., U.S. Pat. No. 6,048,515; Kausch et al., U.S. Pat. No. 5,508,164; Miltenyi et al., U.S. Pat. No. 5,691,208; Molday, U.S. Pat. No. 4,452,773; Kronick, U.S. Pat. No. 4,375,407; Radbruch et al., chapter 23, in Methods in Cell Biology, Vol. 42 (Academic Press, New York, 1994); Uhlen et al., Advances in Biomagnetic Separation (Eaton Publishing, Natick, 1994); Safarik et al., J. Chromatography B, 722: 33-53 (1999); Miltenyi et al., Cytometry, 11: 231-238 (1990); Nakamura et al., Biotechnol. Prog., 17: 1145-1155 (2001); Moreno et al., Urology, 58: 386-392 (2001); Racila et al., Proc. Natl. Acad. Sci., 95: 4589-4594 (1998); Zigeuner et al., J. Urology, 169: 701-705 (2003); Ghossein et al., Seminars in Surgical Oncology, 20: 304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271, which patents are incorporated by reference.

As mentioned above, samples or specimens may be taken from a wide variety of sources for detection or quantification of target polynucleotides with the present invention. Exemplary target polynucleotides include, but are not limited to, nucleic acids from viruses, bacteria, fungus, protozoans, and mammals. In particular, mammalian nucleic acids include cancer genes, such as p53, ATP, Her1 (EGFR), BCR-ABL, PTEN, BRAF, BRCA1, Grb7, topoisomerase IIα, and the like. Exemplary viruses and bacteria containing nucleic acids amenable for detection and/or quantification are listed in Table II. It would be a routine design choice of one of ordinary skill in the art to select target polynucleotides from the organisms of Table II.

TABLE II

Exemplary Viruses and Bacteria

| Viruses | Bacteria |
| --- | --- |
| Human cytomegalovirus (CMV) | Bacillus anthracis |
| Human immunodeficiency virus-1 (HIV-1) | Legionella pneumophilia |
| Enterovirus RNA form cerebrospinal fluids | Listeria monocytogenes |
| Hepatitis C virus (HCV) | Neisseria gonorrhoeae |
| Varicella-zoster virus | Neisseria meningitidis |
| flaviviruses | Xtaphylococcus aureus |
| hepadnaviruses | Helicobacter pylori |
| herpesviruses | Enterococcus faecalis |
| orthomyxoviruses | |
| parvoviruses | |
| papovaviruses | |
| paramyxoviruses | |
| pestiviruses | |
| picornaviruses | |

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims alone with their full scope of equivalents.

What is claimed is:

1. A method of detecting the presence or absence of one or more target polynucleotides in a sample, the method comprising the steps of:

amplifying in a reaction chamber of a reaction system one or more target polynucleotides from the sample using first-stage amplification reagents in a first reaction mixture to form one or more first amplicons, the first-stage amplification reagents including initial primers for each target polynucleotide, wherein the one or more first amplicons are amplified in the presence of a fluorescent indicator capable of generating an optical signal related to a quantity of an amplicon in the first-stage amplification reaction, and wherein the reaction chamber is selectively in fluid communication with a waste reservoir;

monitoring the optical signal of the fluorescent indicator in the first-stage amplification reaction in the reaction chamber;

automatically withholding in the reaction chamber an effective portion of the first reaction mixture and fluidly transferring remainder of the first reaction mixture to the waste reservoir when the optical signal reaches or exceeds a predetermined level;

introducing second-stage amplification reagents into the effective portion of the first reaction mixture to produce a second reaction mixture in the reaction chamber;

amplifying in the reaction chamber the one or more first amplicons in the second reaction mixture, the second-stage amplification reagents including at least one secondary primer for each of the one or more first amplicons, such that each secondary primer is nested in such first amplicon relative to an initial primer of such first amplicon; and detecting the one or more second amplicons to determine the presence or absence of the one or more target polynucleotides in the sample.

2. The method of claim 1 wherein the reaction chamber is a fluidly closed reaction chamber.

3. The method of claim 1 wherein said effective portion is a volume of said first reaction mixture sufficient to contain at least one molecule of said amplicon.

4. The method of claim 3 wherein said effective portion is a volume of said first reaction mixture sufficient to contain at least 100 molecules of said amplicon.

5. The method of claim 4 wherein said first reaction mixture has a volume and wherein said effective portion is a percentage of the volume of said first reaction mixture, the percentage being selected from the range of 0.5 to 10 percent.

6. The method of claim 1 wherein said predetermined level is a multiple of a baseline signal level, the multiple being selected from the range of 1.5 to 25.

7. The method of claim 1 wherein said first-stage amplification reagents and said second-stage amplification reagents include reagents for performing a polymerase chain reaction or a NASBA reaction.

8. The method of claim 7 wherein said fluorescent indicator is selected an intercalating dye that specifically binds to double stranded DNA or comprises an oligonucleotide moiety that specifically binds to an amplification product in said first reaction mixture.

9. The method of claim 8 wherein said one of said one or more amplicons is produced by amplification of a reference sequence in said first reaction mixture.

10. The method of claim 7 wherein said reaction system is a microfluidics device.

11. The method of claim 7 wherein said reaction system comprises:

the reaction chamber selectably in fluid communication with a sample reservoir containing said sample, a first reactant reservoir containing first-stage amplification reagents, and a second reactant reservoir containing second-stage amplification reagents, each of said reservoirs being fluidly closed; and a pump operationally associated with a rotary valve for fluidly transferring said sample and said first-stage amplification reagents to the reaction chamber, for automatically separating said effective portion of said first reaction mixture whenever said optical signal equals or is greater than said predetermined level; and for fluidly transferring said second-stage amplification reagents to the reaction chamber for amplifying said one or more first amplicons in said effective portion.

* * * * *